US007703966B2

(12) United States Patent
Waters

(10) Patent No.: US 7,703,966 B2
(45) Date of Patent: Apr. 27, 2010

(54) WORK LIGHT

(75) Inventor: Michael Waters, Aspen, CO (US)

(73) Assignee: Panther Vision, LLC, West Dundee, IL (US)

( * ) Notice: Subject to any disclaimer, the term of this patent is extended or adjusted under 35 U.S.C. 154(b) by 25 days.

(21) Appl. No.: 12/001,468

(22) Filed: Dec. 11, 2007

(65) Prior Publication Data

US 2008/0130277 A1 Jun. 5, 2008

Related U.S. Application Data

(63) Continuation-in-part of application No. 11/077,682, filed on Mar. 11, 2005, now Pat. No. 7,306,349.

(51) Int. Cl.
*A61B 1/24* (2006.01)

(52) U.S. Cl. ....................... 362/577; 362/227; 362/219; 362/171; 362/186; 362/334; 362/55; 362/102; 362/120

(58) Field of Classification Search ................. 362/227, 362/577, 219, 171, 186, 334, 555, 102, 120
See application file for complete search history.

(56) References Cited

U.S. PATENT DOCUMENTS

| | | | | |
|---|---|---|---|---|
| 1,447,050 | A * | 2/1923 | Stimson | 362/208 |
| 5,036,442 | A | 7/1991 | Brown | |
| 5,321,593 | A | 6/1994 | Moates | |
| 5,339,229 | A * | 8/1994 | Snyder | 362/208 |
| 5,607,227 | A | 3/1997 | Yasumoto et al. | |
| 5,622,423 | A | 4/1997 | Lee | |
| 5,697,695 | A | 12/1997 | Lin et al. | |
| 5,890,794 | A | 4/1999 | Abtahi et al. | |
| D409,776 | S | 5/1999 | Ghode et al. | |
| 5,961,207 | A | 10/1999 | Petkovic | |
| 5,980,063 | A | 11/1999 | Ford et al. | |
| 6,158,882 | A | 12/2000 | Bischoff, Jr. | |
| D436,199 | S | 1/2001 | Lam | |
| D441,888 | S | 5/2001 | Haneda et al. | |
| 6,283,612 | B1 | 9/2001 | Hunter | |

(Continued)

OTHER PUBLICATIONS

"Ferret 30 LED Work Lite 110v", (undated), [online] [retrieved on Nov. 18, 2004] Retrieved from the Internet: http://www.arizonatools.com/catalog/browse/3587-3167-2009-3781/detail/14750, 2 pages.

(Continued)

*Primary Examiner*—Sandra L O'Shea
*Assistant Examiner*—Jessica L McMillan
(74) *Attorney, Agent, or Firm*—Fitch, Even, Tabin & Flannery

(57) ABSTRACT

In one aspect, a light device is provided having an elongate body that has a high strength construction. The high-strength light device is especially well-suited for use as a work light. The work light includes a high-strength body that has a handle and an elongate light-transmissive portion extending from the handle. Preferably, the light-transmissive portion includes a one-piece tubular wall that is tapered and which is molded from a high-strength material. In another aspect, the light device includes anti-rolling surfaces axially between the handle and light transmission portion along the elongate body. The anti-rolling surfaces preferably have a flat configuration so that the flat surfaces keep the elongate body from rolling when placed on a support surface.

22 Claims, 15 Drawing Sheets

U.S. PATENT DOCUMENTS

| | | | |
|---|---|---|---|
| 6,293,684 | B1 | 9/2001 | Riblett |
| 6,527,410 | B2 | 3/2003 | Yamaguchi |
| D473,332 | S | 4/2003 | Lam |
| 6,659,623 | B2 | 12/2003 | Friend |
| 6,676,284 | B1 | 1/2004 | Wynne Willson |
| 6,736,658 | B2 | 5/2004 | Milan |
| 6,739,735 | B2 | 5/2004 | Talamo et al. |
| 6,857,756 | B2 | 2/2005 | Reiff et al. |
| D505,217 | S | 5/2005 | Bayat et al. |
| 6,979,100 | B2 | 12/2005 | Reiff et al. |
| D521,168 | S | 5/2006 | Waters |
| D521,169 | S | 5/2006 | Waters |
| 7,306,349 | B2 | 12/2007 | Waters |
| 2002/0154528 | A1 | 10/2002 | Ravid |
| 2002/0191396 | A1 | 12/2002 | Reiff et al. |
| 2003/0123254 | A1 | 7/2003 | Brass et al. |
| 2004/0062039 | A1 | 4/2004 | Ahn |
| 2004/0228124 | A1 | 11/2004 | Reiff et al. |
| 2005/0265032 | A1 | 12/2005 | Kovacik et al. |

OTHER PUBLICATIONS

"Exlite", (undated), [online] [retrieved on Nov. 18, 2004] Retrieved from the Internet: http://www.finewell.com/eng/Pcat020102.htm, 1 page.

"Rechargeable LED Work Lights", (undated), [online] [retrieved on Nov. 18, 2004] Retrieved from the Internet: http://www.tessco.com/products/displaySkus.do?groupId=585&subgroupId=28, 3 pages.

"BLI Lighting Specialists", (undated), [online] [retrieved on Nov. 18, 2004] Retrieved from the Internet: http://www.budgetlighting.com/store/angora.cgi, 3 pages.

"The LED Traffic Directing Baton Lights", (undated), [online] [retrieved on Nov. 18, 2004] Retrieved from the Internet: http://www.theledlight.com/LEDtrafficbaton.html, 2 pages.

* cited by examiner

WORK LIGHT

CROSS-REFERENCE TO RELATED APPLICATION

This application is a continuation-in-part of prior application Ser. No. 11/077,682, filed Mar. 11, 2005, now U.S. Pat. No. 7,306,349, which is hereby incorporated herein by reference in its entirety.

FIELD OF THE INVENTION

The invention is directed to a lighting device and, more particularly, to an LED work light.

BACKGROUND OF THE INVENTION

Work lights or shop lights are useful lighting devices having wide applications for providing illumination in rugged environments such as workshops, garages, campsites, and many other places. Given the rugged environment in which the lights are used in, it is generally required that the work light have a robust construction such that the light source is not damaged or broken during use.

Common work lights use a variety of different lighting sources to provide illumination. For instance, incandescent or fluorescent light bulbs are common lighting sources used in the work light. While such bulbs are capable of providing sufficient illumination, they have the shortcoming of being fragile and, therefore, requiring relatively large or bulky housings to protect the bulbs from breakage. For instance, incandescent light bulbs, such as a 60-watt light bulb, are often used in work lights, but require bulky, cage structures surrounding the bulb for protection. While the cage may provide limited protection to the bulb, it still does not prevent the bulb from breaking if the work light is dropped. Moreover, the bulky cage structure limits the areas the work light can be used in because its large size prevents the incandescent work light from being used in tight or other confined spaces. Similarly, the fluorescent light bulb, such as the gas-filled, tube light, may be more compact in size than the incandescent bulb, but such bulbs are still very fragile and, therefore, also require extensive protection. In many cases, the protection surrounding the fluorescent light bulb is much larger in terms of its diameter as compared to the diameter of the fluorescent tube itself. As a result, the fluorescent work light also has a limited use in confined spaces. Therefore, while the fluorescent bulb may be narrow, the combination of the bulb or bulbs and required particular housing is quite large, particularly, in the radial direction transverse to the axis of the fluorescent tube.

Other attempts at work lights use LEDs as the light source. The LED or light emitting diode is a very compact and an efficient, solid state light source that is less fragile than incandescent or fluorescent glass lights, but still provides sufficient illumination, especially when several LEDs are grouped together. As a result, work lights using LEDs may be smaller than incandescent or fluorescent work lights, and also generally require smaller housings encasing the LEDs therein. Current work lights that use LEDs as the light source generally seek to take advantage of the sturdier construction of the LED itself and incorporate less robust housings or casings for the lighting device. In that regard, many housings for LED work lights are fabricated from multiple components, which may compromise the integrity and strength of the housing. For instance, in practice it is believed a typical LED work light housing will include a cylindrical casing assembly that surrounds the LEDs via two elongate semi-cylindrical casing parts that are attached at two part lines 180° spaced from each other about the cylindrical casing assembly. Further, a separate end cap is utilized to enclose the free end of the cylindrical casing assembly. By having a three-piece casing assembly, the semi-cylindrical and end cap housing parts can be more readily formed of high strength material; nevertheless, such a configuration can create areas of weakness at the joints or interfaces between the semi-cylindrical casing parts and the end cap attached thereto that compromises the overall strength of the work light. Moreover, such multiple casing components also require more complicated supply chains, the fabrication of more parts, and the additional assembly step of combining all the parts.

When not being held, it is common for the work light to be set down on the floor or a flat, work or support surface like on a table. Prior cylindrically configured work lights can roll when placed down on a flat support surface. Often, in addition to the curved light casing, the work lights also have curved handle surfaces, which may provide a comfortable grip, but also permit the light to easily roll upon a support surface. It can be aggravating to have the work light roll beyond one's reach and potentially damaging to the work light should it be placed on a raised table work surface and then roll thereon to where the work light falls off the table.

Therefore, it is desired to obtain a simplified LED work light having a compact and robust construction. In addition, a work light having a generally cylindrical configuration that does not roll along work surfaces would be desirable.

SUMMARY OF THE INVENTION

In accordance with one aspect of the present invention, a light device is provided having an elongate body that has a high-strength construction. The high-strength light device is especially well-suited for use as a work light as its construction allows it to easily withstand impacts from hitting other hard objects, being dropped, or even run over by an automobile such as can occur when used around workshops, camp sites, and in auto repair facilities. The high strength body includes a handle at one end and a thin elongate light-transmissive portion including a tubular wall that extends from a larger diameter thereof at the handle to a smaller diameter at the other end of the body with a light source contained within an interior space defined by the tubular wall. It has been found that providing the tubular wall of the light transmissive portion with a taper along its length, and particularly along the inner surface thereof, allows the strength of the tubular wall to be optimized by molding the wall from a high strength material and so that it has an integral, one-piece construction.

Generally, prior work lights suggest use of high strength plastic material, but only with constant diameter, cylindrical light heads, which, in practice, require the light heads to have a two-piece construction that can compromise the strength, and particularly the pressure or compressive force resistance of such two-piece light heads. In contrast, the present light device takes advantage of the provision of a taper to the tubular, light-transmissive wall thereof which generally increases the strength of the wall as it progresses down to smaller and smaller diameters since there is more plastic material per unit area of space that the tubular wall encompasses. Moreover, the taper of the tubular wall permits it to be molded with a high-strength material and to have a one-piece, unitary, or integral construction.

It is believed that in practice the high-strength plastic or polymer material, for example, polycarbonate or acrylic plastic, typically has not been molded to form unitary cylindrical walls of the prior light heads because of material shrinkage during molding that makes it very difficult and unduly expensive to remove such a unitary cylindrical part from the mold. By contrast, the tapered, tubular wall of the light device herein allows for it to be molded as a single, unitary component even with high-strength plastic material that experiences significant dimensional shrinkage during molding so that it grips tightly onto part forming mold members. In this regard and as mentioned, it is the inner surface of the tubular wall that is tapered, whereas the outer wall surface may or may not include a taper, since it is the inner surface that is formed by a tapered core pin of the mold with the high-strength plastic material shrinking down and tightly gripping the pin. Nevertheless, by tapering the pin, it can more easily be pulled without having to utilize more complex and expensive molding equipment such as a collapsible core as may be necessitated where a constant diameter cylindrical wall is formed as with prior work light devices. Accordingly, as previously discussed, prior commercial work lights provided with a cylindrical, light-transmissive wall formed from two molded halves that are secured together along two-part lines generally will weaken the light head thereat absent additional fastening hardware that can unduly increase the size and expense thereof. In the present elongate, tapered light head, the light-transmissive tubular wall avoids these problems and provides the wall with its high-strength construction both because of its tapered configuration and by way of its one-piece, unitary construction utilizing high-strength plastic material therefor.

In one form, the light source includes a plurality of aligned LEDs. The use of small LEDs and their alignment is advantageous in keeping the diameters of the tapered, tubular wall to a minimum. In another form, the light source includes a printed circuit board that is inserted into an internal space defined by the tubular wall of the light-transmissive portion. Preferably, the printed circuit board has opposite sides that taper inward toward each other. In this configuration, the printed circuit board generally can have a wedge-type fit in the tapered, tubular wall of the light-transmissive body portion. Preferably, the printed circuit board is elongated and includes the plurality of LEDs aligned along one side of the printed circuit board.

In another form, the tubular wall has a central axis extending therethrough. Preferably, the printed circuit board has a proximate end in the casing aligned with the central axis at the larger diameter of the tubular wall and a distal end that is offset from the central axis at the smaller diameter of the tubular wall. Such configuration of the printed circuit board is advantageous in conjunction with a tapered inner surface of the tubular wall as it permits the aligned LEDs to be of the same size substantially irrespective of their position along the length on one side or surface of the elongate circuit board. In other words, the space between the LED mounting side of the circuit board and the facing portion of the tubular wall at the proximate end can be approximately the same as the corresponding space at the distal end despite the smaller diameter of the casing at the free end of thereof. Also, if the degree of deviation of the circuit board from the casing axis is greater than the taper of the casing wall, then even larger size LEDs can be used toward the distal end of the circuit board.

As mentioned above, the tubular wall has an inner surface and the predetermined taper may be on the tubular wall inner surface. Additionally, the plurality of LEDs may include proximate and distal LEDs with a spacing between a top surface of printed circuit board and the inside surface of the tubular wall. In one aspect of a preferred configuration, even with the tapered tubular wall, the distal LED has a spacing that is about the same as a spacing between the proximate LED and the inside wall surface.

In another form, the tubular wall diameters are optimized for both size and strength advantages. For instance, it is preferred to keep the size of the light-transmissive portion to a minimum for lighting of confined spaces. As a result, in a preferred embodiment, the tubular wall diameters do not exceed approximately 1 inch with an axial length of approximately 14.4 inches; however, longer or shorter light-transmissive portions may utilize larger or smaller diameters. At the same time, while the size is minimized, it is also preferred that the tubular wall have a configuration that is optimized for strength. To this end, the tubular wall may have a ratio of wall thickness to the cross-sectional area that it circumscribes including the internal space about which the wall extends that increases axially along the wall axis from the connection to the handle to the distal end portion. Therefore, such ratio allows the light-transmissive portion to be formed from the high-strength material as described above and, as a result, also have the desired high level of resistance to compressive pressure forces. In one form of the optimized construction, the wall thickness may be constant and the tubular wall may have side portions that taper inward toward each from the connection to the handle to the end portion.

In another form, the handle has a housing that includes openings and fasteners that extend through the openings for connecting the housing together. The printed circuit board generally has a portion that extends into the handle housing and a portion that extends into the light-transmissive portion. Preferably, the printed circuit board also includes openings, which are aligned with the openings of the housing, so that the fasteners may extend therethrough to secure the printed circuit board to the handle. The light transmissive portion may also include a stop between the printed circuit board and the light-transmissive portion that defines a predetermined position of the printed circuit board in the handle housing and the light-transmissive portion such that the respective fastener openings thereof are aligned.

Optionally, the light device may further include a mounting assembly connected to the elongate body. The mounting assembly may be configured for optimized flexibility in mounting the elongate body of the light device to differently configured and constructed mounting surfaces. In this regard, the mounting assembly may include a connector portion of the elongate body, a plurality of different mounting devices for mounting the elongate body to differently configured and constructed mounting surfaces, and a releasable connection between the connector portion and each of the different mounting devices.

In another aspect, the light device may include intermediate anti-rolling surfaces axially between curved surfaces of a forward elongate light head, and a rearward elongate handle of the device with the intermediate anti-rolling surfaces having a generally flat configuration. The flat anti-rolling surfaces keep the light device from rolling when the light device is placed on a flat support surface.

In one form, the casing includes a rearward, radially extending flange having a periphery extending thereabout on which the anti-rolling surfaces are formed. The flange is sized relative to the light head and handle curved surfaces so that one of the flat surfaces thereof will engage the support surface when the body is placed thereon. In another form, corner projections are formed between adjacent flat surfaces with the corner projections extending radially beyond the curved surfaces of the casing and the handle.

In a preferred form, the handle curved surface has a varying radius of curvature and includes corner surface portions and support surface portions. The corner surface portions are between adjacent support surface portions and have a radius of curvature larger than the curved corner surface portions. Each of the curved support surface portions of the handle are circumferentially aligned with one of the flat anti-rolling surfaces. In this manner, the light device includes two distinct areas of contact that are axially spaced from each other along the device so that when placed on a support surface, the device will not roll thereon, with one of the areas being at one of the flats and the other area being at the corresponding aligned curved support surface portion of the handle. The handle support surface portions cooperate with the flat anti-rolling surfaces to provide the work light body with additional stability against rolling when it is placed on the support surface.

In another form, the light device includes an elongate body having a tubular light transmission casing, an elongate handle, and an intermediate nut having flats with the nut disposed between the casing and the handle. The nut is sized so that when the elongate body is placed on a flat support surface, one of the nut flats will engage flush on the support surface to keep the body curved surfaces from rolling on the support surface.

In one form, the curved surface of the casing has a substantially constant radius of curvature, and the nut is radially enlarged relative to the casing so that the flats thereof project beyond the casing curved surface.

In a preferred form, the casing is tapered to have a large diameter end adjacent the intermediate nut tapering down to a small diameter distal end of the casing, and the nut has an octagonal configuration so that there are eight flats thereof. With the octagonal configuration, the nut can be sized so that each of the flats thereof only project beyond the curved surface of the adjacent, casing large diameter end by a minimal amount.

DETAILED DESCRIPTION OF THE PREFERRED EMBODIMENTS

Figure 1:
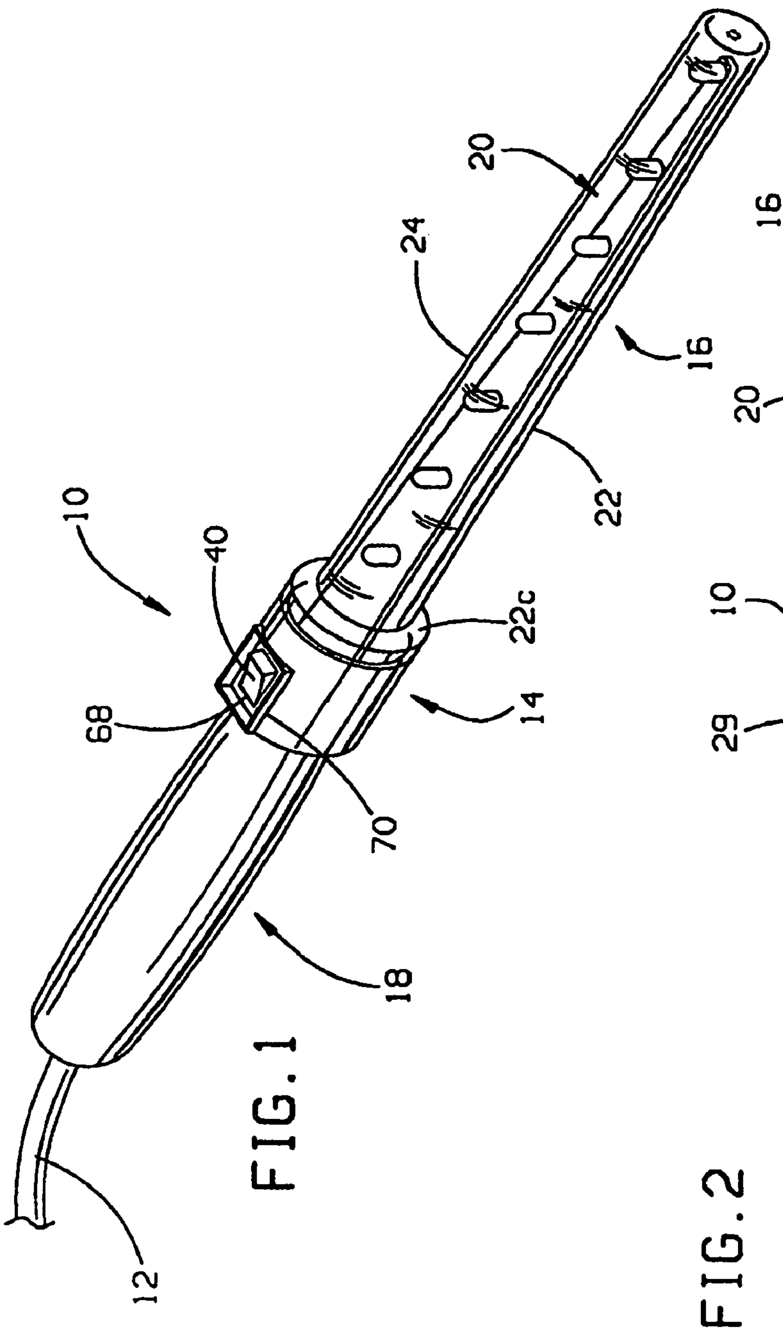
FIG. 1 is a perspective view of a light device in accordance with the present invention showing a handle and an elongate light-transmissive portion extending therefrom.
Figure 2:
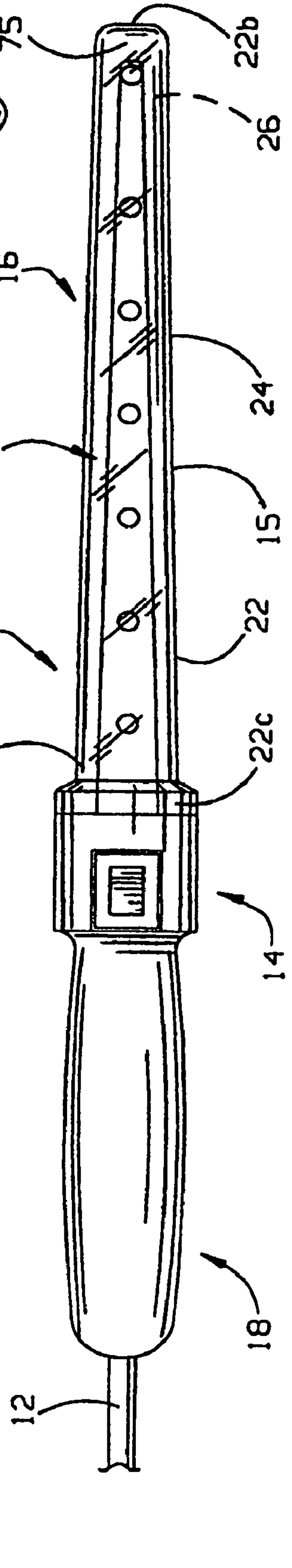
FIG. 2 is a plan view of the light device of FIG. 1 showing a taper of the light transmissive portion and LEDs aligned on a circuit board in the tapered light transmissive portion.

In FIGS. 1 and 2, an LED work light 10 is shown that is provided with a high-strength construction in accordance with the present invention. The light 10 may be powered from a standard 110 volt wall outlet through a cord 12 plugged into the outlet in a known manner. Battery powered and combination units providing options in terms of powering the light device with either power from a wall outlet or a battery are also contemplated. The batteries can be rechargeable. Further, the cord 12 can be provided with a connector that allows it to be plugged into a typical cigarette lighter in a vehicle to be powered by the electrical power source thereof. In this regard, the power cord 12 can be provided in different lengths on different light units 10 such as with a twenty foot length for automobiles or a forty foot length for trucks.

In general, the light 10 includes a high-strength, elongate body 14 including an elongate, light head 15 having a substantially light-transmissive portion or casing 16, and a handle portion 18 from which the light head 15 including its light-transmissive portion 16 extends. A light source 20 of the light head 15 is generally disposed in the light-transmissive portion or casing 16 in such a manner to emanate light therethrough.

To provide the high-strength construction, the light-transmissive portion 16 is fabricated from a high-strength material and includes a one-piece tubular wall 22 that has an elongate axis Z extending therethrough and an annular side wall portion 24 extending thereabout that is tapered relative to the axis Z. The tapered sidewall portion 24 allows the tubular wall 22 to be molded from a high strength material in one piece rather than being molded as multiple components as has previously been described. As will be discussed further hereinafter, the taper may be provided only along an inner surface 28 of the side wall portion 24 to achieve the strength advantages described herein, although the illustrated side wall portion 24 also includes a taper on an outer surface 30 thereof as well.

As best seen in FIGS. 1-5, the light-transmissive portion 16 is a generally elongate tubular structure that includes the one-piece tubular wall 22 having a transverse end wall portion 22*b* integrally formed with the side wall portion 24 at the distal free end thereof. At the other end of the side wall 24, an integral flange or shoulder wall portion 22*c* can be formed. Therefore, the side wall portion 24 extends axially from the shoulder wall portion 22*c* to the end portion 22*b* to form the elongate tubular casing 16, which is closed at the distal end thereof by the end wall portion 22*b*. Accordingly, portions 24 and 22*b* define an interior space 26 that can receive the light source 20 therein.

Axially opposite the distal end portion 22*b* is the proximate shoulder wall portion 22*c*, which extends or flares radially outwardly from the side wall portion 24 to connect with the handle 18. The outward extending shoulder portion 22*c* provides further strength enhancement to the casing 16 due to its flanged construction providing the casing 16 with a greater radial thickness of the high-strength material at the joint interface between the casing 16 and the handle 18. As shown, the casing sidewall 24 preferably tapers down from a large diameter handle connecting end 29 to the distal end wall 22*b* so that the largest diameter X is at the connecting end and the smallest diameter Y is at the distal end of the casing. The shoulder portion 22*c* also includes a connecting structure 22*d* for connecting the light-transmissive portion 16 to the handle 18. The connecting structure 22*d* may include an annular tongue or rib 23 and an annular groove 21 between the rib 23 and a rearwardly facing surface 19 of the radially enlarged wall portion 22*c*. The rib 23 has an end stop surface 71 used for positioning the light source 20 within the interior space 26, as will be described further hereinafter. The groove 21 also includes a key tab or protrusion 73 for mating with a notch 75 in the handle 18. The protrusion 73 fixedly, circumferentially orients the light-transmissive portion 16 relative to the handle 18, as will be further described below.

In the preferred and illustrated form, the tubular wall 22 has a generally constant thickness 25 with the tapers of the wall surfaces 28 and 30 being the same, e.g., 0.10 inch. The tapered side wall portion 24 has a diameter of about 1 inch at the wall outer surface 30 at connection end 29 tapering down to a diameter of about 0.7 inch at the wall outer surface 30 at end portion 22*b*. As shown, the distal end wall portion 22*b* can also be of the same thickness as the side wall portion 24 so that the tubular casing 16 is of substantially constant thickness except at the connecting end structure 22*c* thereof.

The tapered casing configuration is advantageous in terms of the strength enhancement it provides the present work light 10. As previously mentioned, molding the light-transmissive portion 16 of high strength material while keeping it as a unitary component is extremely difficult. However, herein such molding is readily accomplished by providing the sidewall portion 24 with the aforedescribed tapered configuration in contrast to the cylindrical shapes of prior work light casings. Accordingly, the present casing 16 is formed of high-strength polymer material and does not include part lines extending therealong which can create areas of weakness in a work light.

A further strength advantage obtained by the tapered sidewall portion 24 for the light-transmissive portion 16 herein is achieved by the greater concentration of the rigid wall material in a progressively smaller space as the wall 24 tapers down towards its smaller diameter end 31. As previously described, the wall 24 tapers from the larger proximate end 29 down to the smaller diameter distal end 31 so that the wall 24 provides increasing strength down toward its distal end. In other words, because there is progressively more plastic material in a smaller and smaller cross-sectional area of the light head 15, there is more resistance to breakage due to impacts and compressive forces as the ratio of the wall thickness of the casing 16 to the cross-sectional area circumscribed by the casing wall 24 increases. For instance, with a constant thickness casing wall 24, this ratio will be greatest at the distal end 31 of the casing 16 because of the taper of the side wall to its smallest diameter Y thereat so that the light head cross-sectional areas defined by the formula $\Pi r^2$ is also the smallest, whereas at the handle connecting end 29, the diameter X and thus the light head cross-section area is largest decreasing the ratio to its smallest extent.

Figure 21:
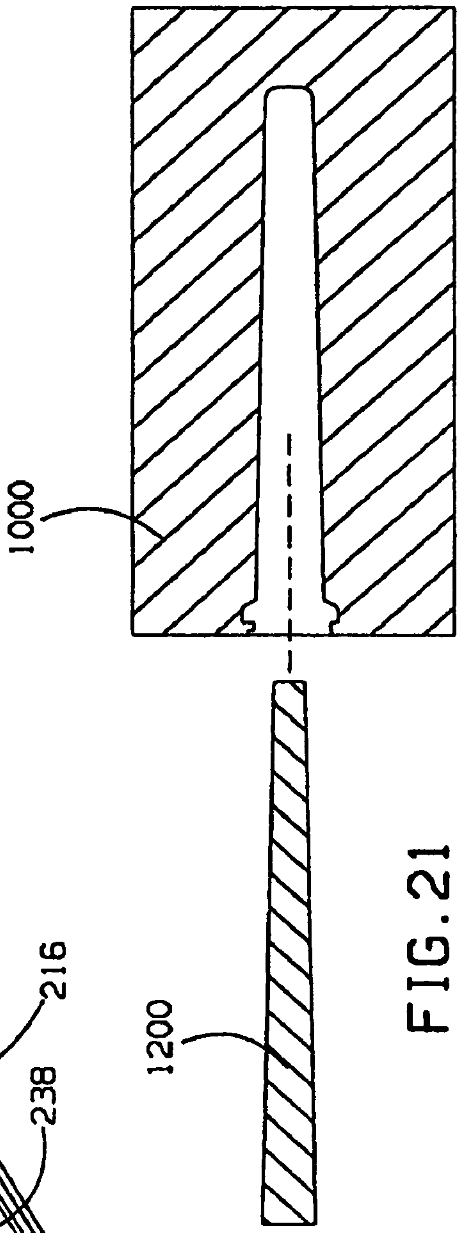
FIG. 21 is a sectional schematic of an exemplary cavity mold and core pin for molding the one-piece tubular casings portions of the present light devices.

As discussed above, the taper of the side wall portion 24 is preferred because it allows both high strength material to be utilized for the casing 16 and to form it with a one-piece construction, which also provides high strength to the light 10 herein, and particularly the casing portion 16 thereof. To this end, molding the casing 16 in one piece from a high-strength material can be done in a relatively straight forward and inexpensive molding process employing a tapered cavity mold 1000 and a tapered core pin 1200 (FIG. 21). The use of complicated mold components such as collapsible cores and the like is avoided even though molding with high strength material. The high-strength material may be any moldable, high-strength material that allows light transmission therethrough such as polycarbonate or acrylic polymer materials. For example, it is believed that with the present tapered casing 16 formed of polycarbonate material, the casing 16 will be capable of withstanding a compression force at least about 500 pounds per square inch with strengths of greater than 2000 pounds per square inch also being achievable.

Figure 3:
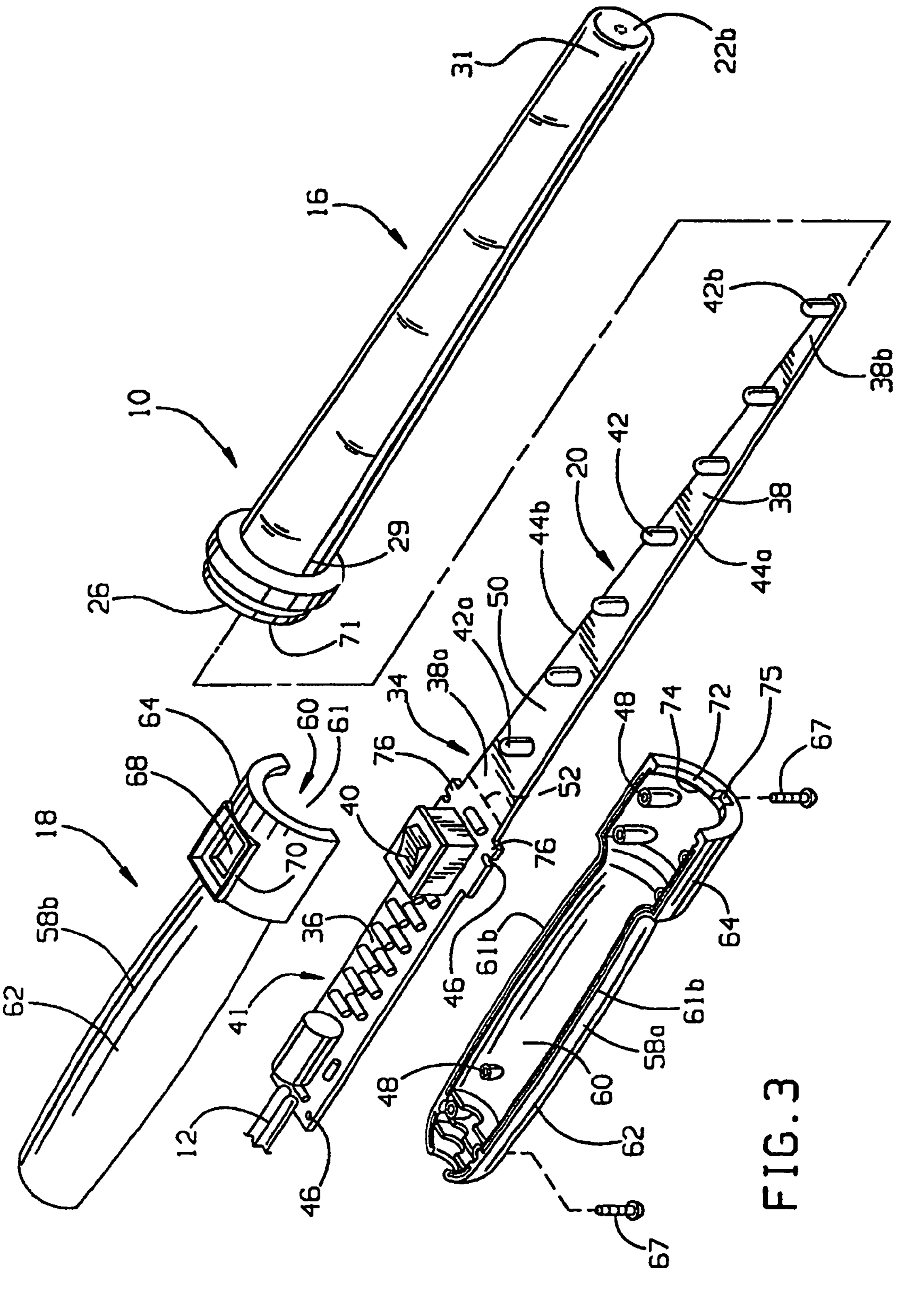
FIG. 3 is an exploded, perspective view of the light device of FIG. 1 showing the light-transmissive portion formed as a one-piece tubular casing and the handle having a two-piece construction with the circuit board including portions in both the handle and the casing.
Figures 4A, 4B, 4C, 6:
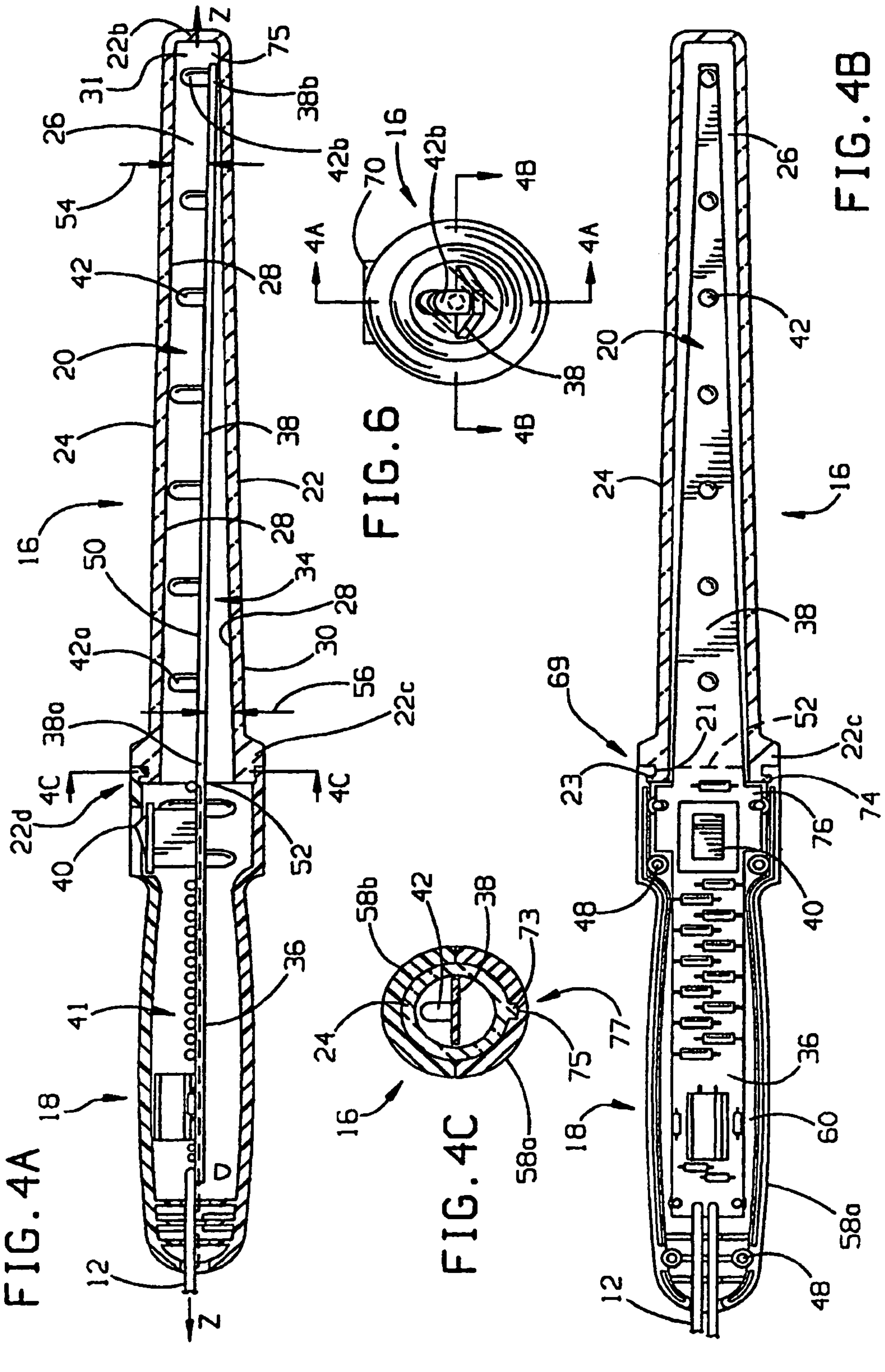
FIG. 4A is a side elevation view partially in section generally taken along line 4A-4A in FIG. 6 showing the circuit board extending offset to the axis of the tapered casing.
FIG. 4B is a cross-sectional view generally taken along line 4B-4B in FIG. 6 showing the connection of the handle, the light-transmissive portion, and the circuit board.
FIG. 4C is a cross-sectional view taken along like 4C-4C of FIG. 4A showing anti-rotation structure in engagement between the casing and the handle.
FIG. 6 is a front, elevational view of the light device of FIG. 1 showing the taper of the circuit board.
Figures 5, 7, 8, 9:
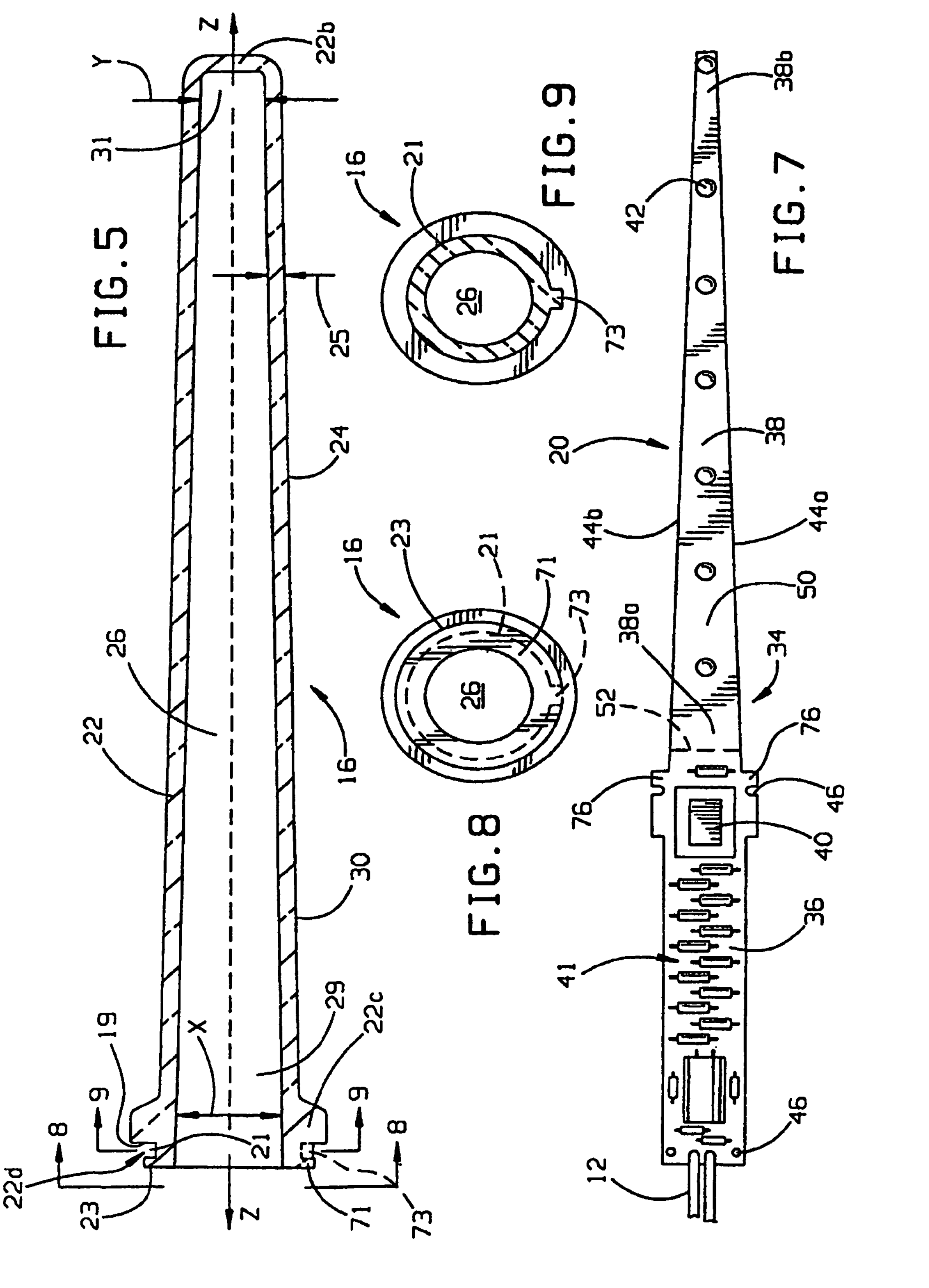
FIG. 5 is an enlarged, cross-sectional view of the tubular casing portions of FIG. 3 showing the taper and constant thickness of the side wall portion of the casing.
FIG. 7 is a plan view of the printed circuit board of FIG. 3 showing tapered side edges thereof.
FIG. 8 is a rear, elevational view of the tubular casing taken along line 8-8 in FIG. 5.
FIG. 9 is a cross-sectional view taken along line 9-9 in FIG. 5.
Figure 10:
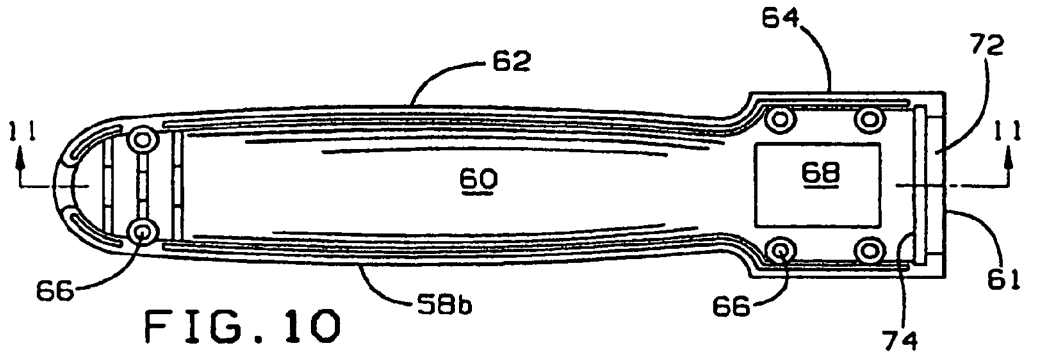
FIG. 10 is a plan view of one of the handle members of the two-part handle housing.
Figure 11:
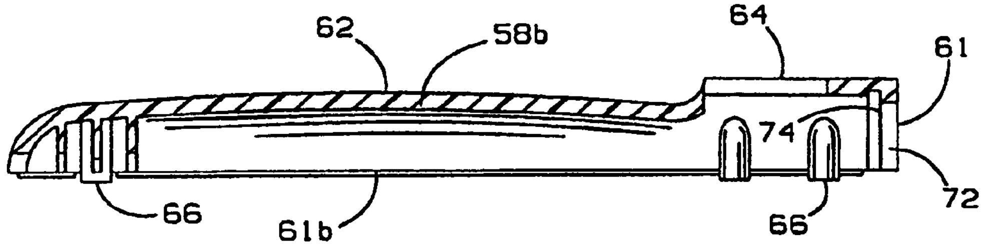
FIG. 11 is a cross-sectional view of the handle member generally taken along line 11-11 in FIG. 10.

Referring to FIGS. 3, 4A, and 7, the preferred light source 20 will next be described. The light source 20 generally includes an elongate printed circuit board 34 having an electronics receiving base portion 36 and an elongate, illumination portion 38 extending therefrom. The electronics receiving base portion 36 has the power cord 12 connected thereto, an on/off switch 40, and other electrical components 41 for providing electrical power to the light source carried thereon.

As shown, switch 40 is a rocker-type switch; however, other switching devices may also be used. The components 41 can include various diodes, capacitors, and resistors that convert the 110 volt AC obtained from the wall outlet via the power cord 12 to about 30 volt DC for energizing the LEDs 42. Manifestly, these electrical components and/or circuitry can be varied to accommodate light units 10 adapted to be plugged into cigarette lighters or for those that utilize battery power.

The electronics receiving base portion 36 of the circuit board 34 is disposed within the hollow handle 18 of the light 10. As best illustrated in FIGS. 3 and 7, the circuit board base portion 36 may include one or more fastening structures 46 that mate with one or more corresponding fastening structures 48, 66 in the handle 18. Preferably, circuit board fastening structures 46 are recess openings and/or apertures in the electronics receiving base portion 36 that can be aligned with the fastening structures 48, 66 in the form of annular bosses in the handle 18. Protrusions or abutments 76 of the circuit board 34 are provided at a predetermined position along the length of the circuit board 34 so that when brought into engagement with the casing stop surface 71, the circuit board fastening structures 46 are aligned with the handle fastening structures 48, 66. Each of the fastening structures 46 and 48, 66 are sized to allow a fastener 67, such as a screw, rivet, or the like, to extend therethrough to secure the circuit board 34 in the handle 18 and casing 16, and the electronics receiving base portion 36 to the handle 18 and, more specifically, to keep the circuit board base portion 36 from shifting axially relative to the handle 18. In this manner, the circuit board 34 is axially fixed in the hollow body 14 of the light device 10 when the handle members 58*a* and 58*b* are fastened together. Further, the aligned bosses 48, 66 of each of the handle members 58*a* and 58*b* define a small gap therebetween when the members 58*a* and 58*b* are connected. The thickness of the circuit board 34, and specifically the base portion 36 thereof, fits in this small gap so that the base portion 36 generally extends centrally in the handle cavity along the central axis Z aligned with the part lines 61*a*, 61*b* on either side thereof formed between the connected handle members 58*a* and 58*b*.

The elongate circuit board portion 38 includes an illumination source 42, which is preferably a plurality of LEDs. Conductive traces formed on the printed circuit board 34 electrically interconnect the LEDs with the power source via on/off switch 40, the electrical components 41, and the power cord 12. It is preferred that LEDs be aligned along the circuit board as shown in FIG. 7 to keep the diameters of the light-transmissive portion 16 to a minimum. In particular, the aligned LEDs allow the smallest diameter Y of the casing 16 to be minimized in size. As illustrated in FIG. 7, the LEDs 42 are also preferably disposed on a single surface 50 of the illumination portion 38 which also assists in keeping the light-transmissive portion 16 size to a minimum. In addition, the single side arrangement of the LEDs 42 on the printed circuit board 34 maximizes the light emanated from the light transmissive portion 16 from one side thereof.

As illustrated in FIGS. 3, 4B, and 7, the illumination portion 38 of the circuit board 34, like the casing 16, also has an elongate configuration and, preferably, has side edges 44*a* and 44*b* that taper inward toward each other from the electronics receiving base portion 36 to a distal end 38*b* of the illumination portion 38. In this configuration, the illumination portion 38 is received in the interior space 26 of the light-transmissive portion 16 and may have a generally wedge fit in such space. The side edges 44*a* and 44*b* may be frictionally received in the interior space 26 such that the edges 44*a* and 44*b* contact the inside surface 28 of the tubular wall 22 when the circuit board portion 38 is fully received in the casing 16. For this purpose, the taper of the side edges 44*a* and 44*b* generally corresponds to the taper of the sidewall portion 24 of the tubular wall 22. Therefore, in addition to providing high strength, the taper of the side wall portion 24 may also aid in the positioning and/or securing of the light source 20 in the interior space 26. Alternatively, there may be a slight clearance between the circuit board edges 44*a* and 44*b* and the casing wall 24, but the cooperating tapered configuration of each assists in positioning the illumination portion 38 in the interior space 26 generally laterally centered relative to the central, longitudinal axis Z, but preferably offset therefrom as will be described hereinbelow. In either case, the wedge-fit makes insertion of the circuit board portion 38 in the casing 16 easier since the smallest width distal end 38*b* thereof is the leading end that is initially inserted in the largest diameter end of the casing tapered interior space 26.

The printed circuit board 34 may also have a transition section 52 at which the illumination portion 38 is angled away from the electronics receiving base portion 36. Generally, the transition or bent section 52 can take the form of a transverse bend line 52 between the base and illumination portions 36 and 38 of the circuit board 34. As previously mentioned, the base portion 36 is captured by the internal projections or bosses 48 and 66 in the handle 18 to extend centrally therein. Accordingly, when assembled in the casing 16, the illumination portion 38 will generally extend transversely at an oblique angle to the longitudinal axis Z. Thus, when received in the interior space 26, the illumination portion 38 has a proximal end 38*a* adjacent the portion 36 that is generally aligned with the central longitudinal axis Z as is the electronics receiving base portion 36 itself, and a distal end 38*b* that is offset from the longitudinal axis Z. In other words, when received in the interior space 26 of the light-transmissive portion 16, the proximal end 38*a* is aligned with the longitudinal axis Z near the shoulder wall portion 22*c* and the distal end 38*b* is above or below the axis Z near the end portion 22*b*. Such angled configuration of the illumination portion 38 relative to the electronics receiving base portion 36 generally permits the LEDs 42 to be of the same size substantially irrespective of the position of the LEDs 42 along the length of the printed circuit board 34.

As shown, the illumination portion 38 extends substantially linearly in the casing interior space 26 but at a greater angle of deviation from the axis Z than the sidewall 24. In this manner, a space 54 between the LED mounting surface 50 of the illumination portion 38 and the facing side of the inside casing wall 28 will become progressively larger as the illumination portion 38 extends distally in the interior space 26. This allows the size of the distal LED 42*b* to be just as large as the proximate LED 42*a*, or even larger if desired. On the other hand, a space 56 between the opposite side of the illumination portion 38, which does not include LEDs 42, and the inner wall surface 28 will become progressively smaller as the illumination portion 38 extends distally in the interior space 26. As is apparent, the angle of the illumination portion 38 can be the same as the taper of the casing wall 24 so that the LEDs 42 can be of the same size since the space 54 between the board surface 50 and the casing wall 24 also stays the same along the length thereof.

A stop 69 between the circuit board 34 and casing 16 is preferably provided which defines how far the printed circuit board 34 extends into the interior space 26 of the casing 16. As shown in FIGS. 3 and 4, the stop 69 includes the stop surface 71 of the casing 16 and the abutment tabs 76 of the circuit board 34 to define a predetermined position of the circuit board illumination portion 38 within the interior space 26 of the light-transmissive portion 16. The casing stop surface 71 has an annular configuration with an inner diameter that is smaller than the distance across the laterally extending tabs 76. Accordingly, when the circuit board illumination portion 38 is inserted into the interior space 26, the casing stop surface 71 and the protrusion tabs 76 on the electronics receiving base portion 36 (FIGS. 3 and 4B) interfere with each other to abuttingly engage and define the predetermined longitudinal or axial position of the circuit board portion 38 in the casing 16. Preferably, the protrusion tabs 76 are disposed on the electronics receiving base portion 36 adjacent the transition section 52 such that when inserted in the light 10, the predetermined longitudinal position of the circuit board base portion 36 is entirely within the handle 18 and the illumination portion 38 is disposed entirely in the casing 16 with a predetermined small gap 75 between the distal end 38*b* of the board 34 and the end wall portion 22*b* of the casing 16 (FIGS. 2 and 4B). Preferably, the gap 75 is ¼ inch or less.

Referring to FIGS. 3 and 10-13, the handle 18 will now be described in more detail. In the preferred and illustrated form, the handle 18 includes two shell members 58*a* and 58*b* that are secured together to form the hollow handle 18 having a cavity 60 for receiving the electronics receiving base portion 36 of the light source 20 as previously described. The shell members 58*a* and 58*b* cooperate to form a gripping portion 62 and a mounting portion 64 of the handle 18. Preferably, the gripping portion 62 is contoured to have a slight curve or bulge as it extends axially and sized to comfortably fit in a user's hand. The mounting portion 64 is slightly radially enlarged relative the gripping portion 62 and configured to be connected with the connecting portion 22*d* of the casing 16. As illustrated, the mounting portion 64 includes an annular rib 72 that projects radially inwardly, and an annular groove 74 adjacent the rib 72 to interfit with the annular groove 21 and rib 23 of the casing connecting portion 22*d*. More particularly, when the handle members 58*a* and 58*b* are properly fastened together, the rib 23 of the casing portion 22*d* fits in the handle groove 74, and the handle annular rib 72 fits in the casing annular groove 21.

Figure 12:
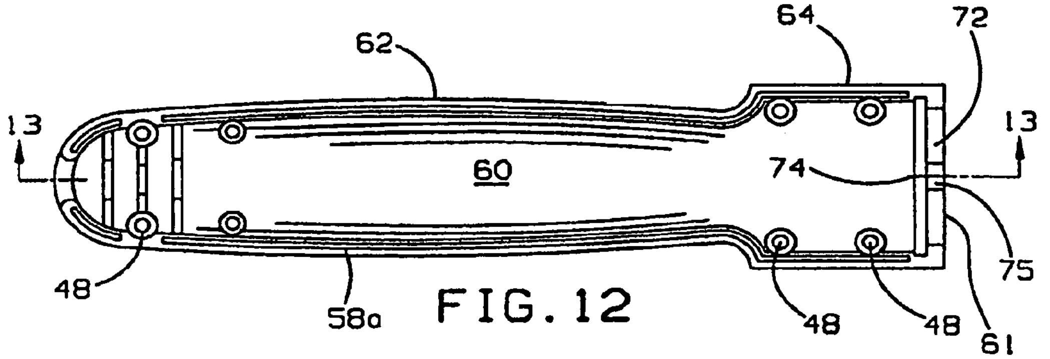
FIG. 12 is a plan view of the other handle member of the two-part handle housing of FIG. 3.
Figure 13:
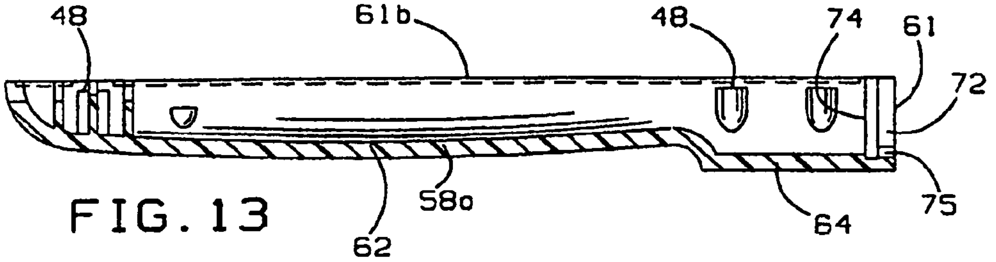
FIG. 13 is a cross-sectional view of the other handle member generally taken along line 13-13 in FIG. 12.
Figure 14:
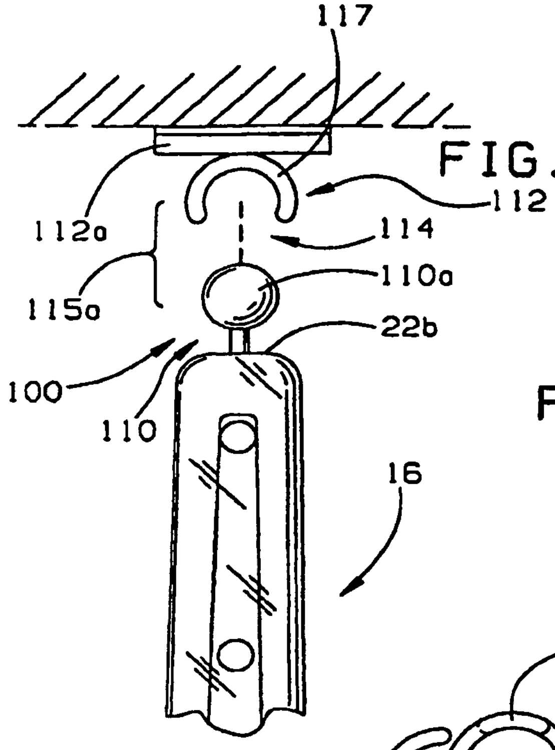
FIGS. 14-16 are enlarged, fragmentary views of the casing distal end portion showing mounting assemblies including a ball and socket releasable connection between the casing portion and different mounting devices.
Figure 15:
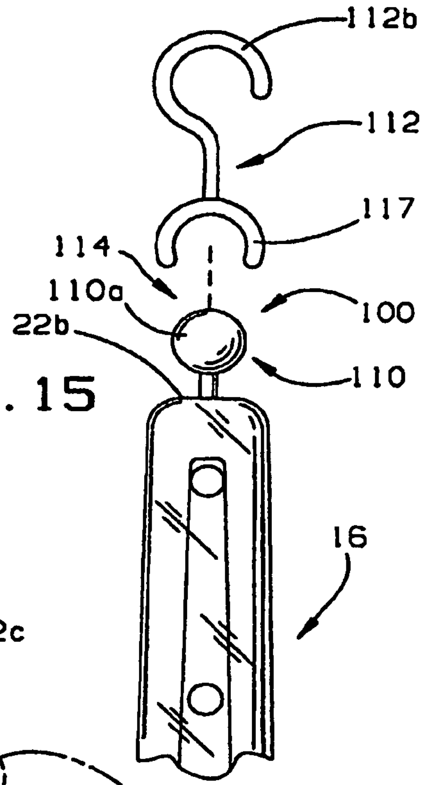

To keep the casing 16 from rotating relative to the handle 18, anti-rotation structure 77 is provided therebetween. More particularly, so that the ribs 23, 72 do not turn in their respective annular grooves 21, 74 in which they seat, a radially outwardly projecting tab 73 of the casing connector 22*d* is configured to seat in a notch 75 of the handle connector 64. Manifestly, the tab 73 could instead be on the handle connector 64 and the notch 75 formed on the casing connector 22*d*. Referring to FIGS. 3, 5, and 12, it can be seen that as illustrated that the tab 73 is in the casing annular groove 21 and the notch 75 is formed in the handle annular rib 72. It should be also noted that until the casing 16 is properly circumferentially aligned relative to the handle 18 to position the tab 73 in alignment with the notch 75, the handle member 58 and 58*b* will not be able to be properly secured together so as to be clamped along their part lines 61*a* and 61*b*.

As previously mentioned, the shell members also include fastening structures in the form of integral annular bosses formed in the respective shell members 58*a* and 58*b*. While the bosses 48 define through holes through which the screw fasteners 67 extend, the bosses 66 are internally threaded blind bosses that do not open to the exterior surface of the handle member 58*b*.

The assembly of the preferred light device 10 will next be described. To secure the shell members 58*a* and 58*b* together with the circuit board electronics receiving base portion 36 therebetween, the corresponding fastening structures 46, 48, and 66 are longitudinally aligned along axis Z via the stop 69. More particularly, the circuit board illumination portion 38 is first advanced into the interior space 26 of the casing 16 until the circuit board protrusions 76 engage the casing stop surface 71. The taper of the circuit board 34 assists in fitting the board 34 in the casing 16 as previously discussed and the edges 44*a*, 44*b* thereof can engage the casing inner surface 28 or be closely adjacent thereto with the board 34 fully inserted to provide a wedge fit of the board 34 in the casing. Then the handle members 58*a* and 58*b* are clamped together around the exposed base portion 36 of the circuit board 34. First, the handle member 58*a* is circumferentially oriented so that the notch 75 is aligned with the casing tab 23. Then, the casing rib 23 is seated in the half of the groove 74 in the handle member 58*a* with the half of the rib 72 in the handle member 58*a* being fully seated in the casing groove 21. In this manner, the apertures and recess 46 of the circuit board base portion 36 are aligned with the corresponding bosses 48 of the handle member 58*a*. Next, the shell 58*b* is clamped on the shell 58*a* in a similar manner with the casing rib 23 seated in the other half of the groove 74 in the handle member 58*b* and the other half of the rib 72 in the handle member 58*b* seated in the casing groove 21. In this arrangement, the bosses 66 of the handle member 58*b* will also be aligned with the circuit board recesses and apertures 46 and handle bosses 48. Finally, the fasteners 67 are inserted through the aligned fastening structures 46, 48, and 66 to secure the components together. When secured together, the handle shells 58*a* and 58*b* define a generally hollow structure defining the handle cavity 60 that is closed at one end and has an opening 61 at the other end. The printed circuit board 34 extends through the opening 61 after being secured within the handle.

The shell members 58*a* and 58*b* are generally mirror images of each other that preferably only have minor differences therebetween. For example, the shell member 58*b* preferably includes an opening 68 sized to receive the on/off switch 40 mounted on the printed circuit board 34. As best shown in FIG. 1, the on/off switch 40 protrudes through the opening 68 when the shells 58*a* and 58*b* and printed circuit board 34 are assembled as previously described. To limit the instances of inadvertent switching, the opening 68 has a flange 70 extending thereabout so that the switch 40 is surrounded thereby.

Referring to FIGS. 14-18, a mounting assembly 100 for mounting the light device 10 to a variety of different configurations and constructions of mounting surfaces or members is depicted. In general, the mounting assembly 100 includes a connector portion 110, a plurality of different mounting devices 112, and a releasable connection 114, which allows the mounting devices 112 to be readily interchanged for use with the light device 10 depending on what it is to be mounted to. In this manner, the light device 10 is provided with flexibility in being able to be mounted in different locations and environments of use to provide hands-free illumination of a wide variety of work areas.

More specifically, the releasable connection 114 can be in the form of a ball-and-socket joint 115 with the connector portion 110 extending outwardly from the end wall portion 22*b* of the casing 16 and having a ball member 110*a* formed at the free end thereof. The mounting devices 112 can each include a resilient arcuate clip 117 that is configured to tightly grip onto the ball member 110*a*. As shown, resilient clip 117 can have a C-shaped configuration so that it can snap on and off the ball member 110*a*. In this manner, the mounting assembly 100 preferably provides a universal or other "quick" connect feature so that a variety of different mounting devices 112 can be mounted to the same light connector portion 110.

Figure 17:
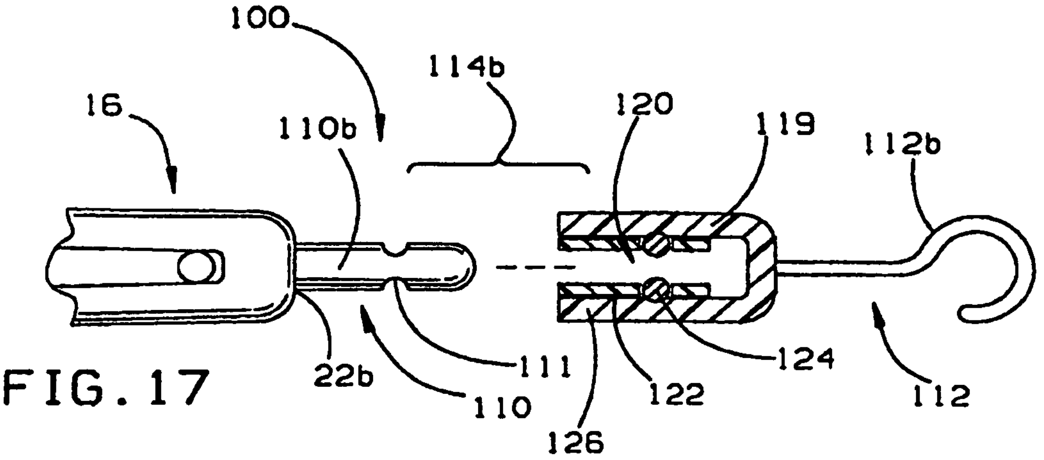
FIG. 17 is an enlarged, fragmentary view of the casing distal end portion showing an alternative mounting assembly.
Figure 18:
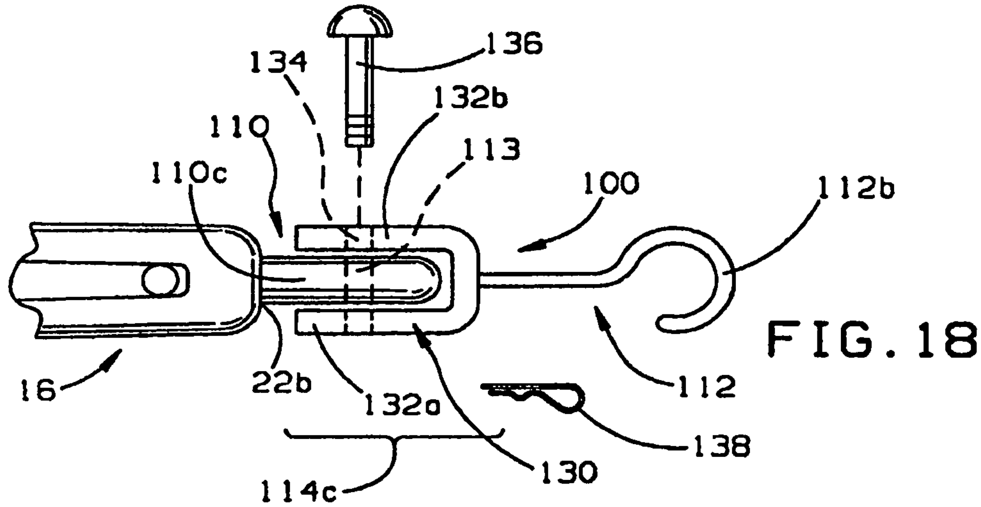
FIG. 18 is an enlarged, fragmentary view of the casing distal end portion showing an another alternative mounting assembly.

Instead of the ball-and-socket type quick connect 115, alternatively, the connector portion 110 may be either a pin 110*b* having a locking groove 111 (FIG. 17) or a pin 110*c* having a through aperture 113 (FIG. 18). Referring to FIG. 17, the mounting device 112 can include a resilient sleeve member 119 in which a ball-bearing assembly 120 is held. The race 122 of the ball-bearing assembly 120 is press-fit into the sleeve 119. The balls 124 generally are in interference with the outer diameter of the pin 110*b* so that inserting the pin 110*b* into the open-ended sleeve 119 will cause the sleeve wall 126 to deflect outwardly until the groove 111 is aligned with the balls 124 which then snap into the groove 111 to releasably connect the mounting device 112*b* of FIG. 17 to the light device 10. The other mounting devices 112*a* and 112*c* can also be provided with the sleeve member 119.

In FIG. 18, the mounting device 112 also includes a connector sleeve member 130; however, it can be of more rigid construction than the resilient sleeve member 119 of FIG. 17. The arms 132*a* and 132*b* of the sleeve member 130 have aligned apertures 134 for being brought into alignment with the pin through aperture 113 as shown. A fastener 136 is then inserted through the aligned apertures and is held at its projecting end by a cotter pin 138 so that the mounting device 112*b* of FIG. 18 is releasably connected to the light device 10. The other mounting devices 112*a* and 112*c* can also be provided with the sleeve member 130.

Figure 16:
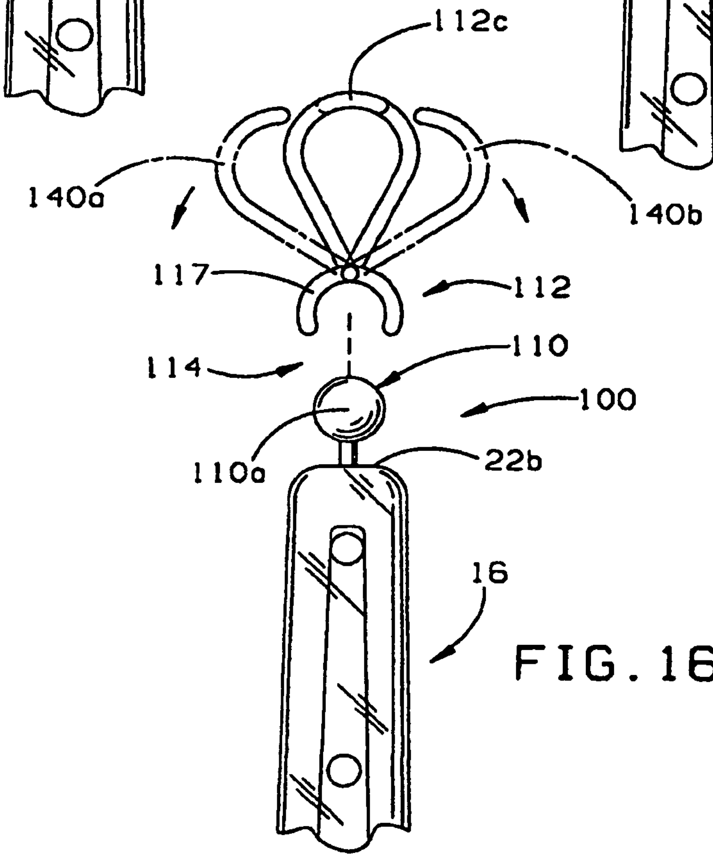

The mounting device 112 may be a variety of different structures designed to mount to a variety of differently constructed or configured mounting surfaces or members. For instance, mounting device 112 may include a magnet 112*a* (FIG. 14), an open hook 112*b* (FIGS. 15, 17-18), or a pinching-type hook 112*c* (FIG. 16). The magnet mounting device 112*a* is useful for hanging the light device 10 from a metallic surface such as from under an automobile hood, to its undercarriage, or to the underside of a shelf. The hook mounting device 112*b* can mount the light device 10 to rest along power cords or in apertures or over edges of other structures. The hook 112*c* has spring loaded arm members 140*a* and 140*b* that are biased to a closed position to provide more secure mounting of the light device to an object extending through the closed hook device 112*c*. While the figures illustrate exemplary mounting devices 112, such devices can be any other known devices that will mount an object to a mounting surface or mounting member.

Each mounting device also includes a portion that connects with the connector portion 110 such that the mounting device 112 and the connector portion 110 also form the releasable connection 114 as previously described. The releasable connection 114 is designed to allow the variety of different mounting devices 112 to be quickly connected to and disconnected from the connector portion 110. Therefore, only one connector portion 110 is necessary to accommodate the variety of mounting members 112.

Figure 19:
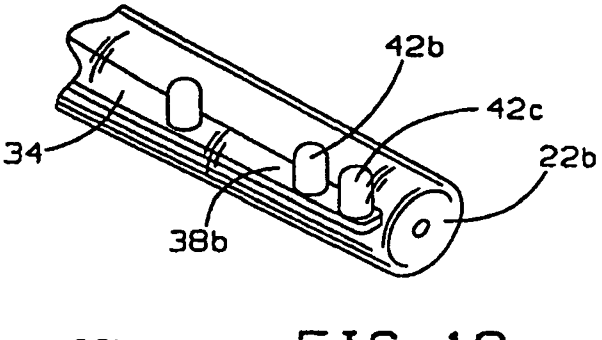
FIGS. 19-20 are enlarged, fragmentary views of the casing distal end portion showing alternative LED arrangements.
Figure 20:
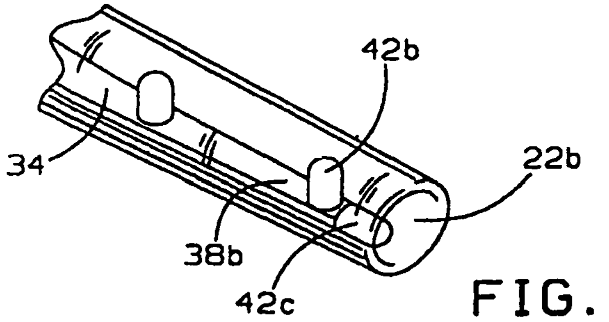

Referring to FIGS. 19-20, alternate configurations of the LEDs 42 on the distal end 38*b* of the circuit board 34 are illustrated. For instance, FIG. 19 shows an arrangement having two closely spaced LEDs 42*b* and 42*c* that are aligned on the circuit board surface. This arrangement provides more concentrated light at the distal end of the light device 10. Alternatively, as shown in FIG. 20, the distal end 38*b* of the circuit board 34 may include the additional LED 42*c* oriented at a right angle or orthogonal to the other LEDs to extend along the axis Z directed toward the casing end wall 22*b*. This allows the light device 10 to be used as a more traditional flashlight as light also emanates from the elongate light device 10 in the direction it is pointed.

Figure 22:
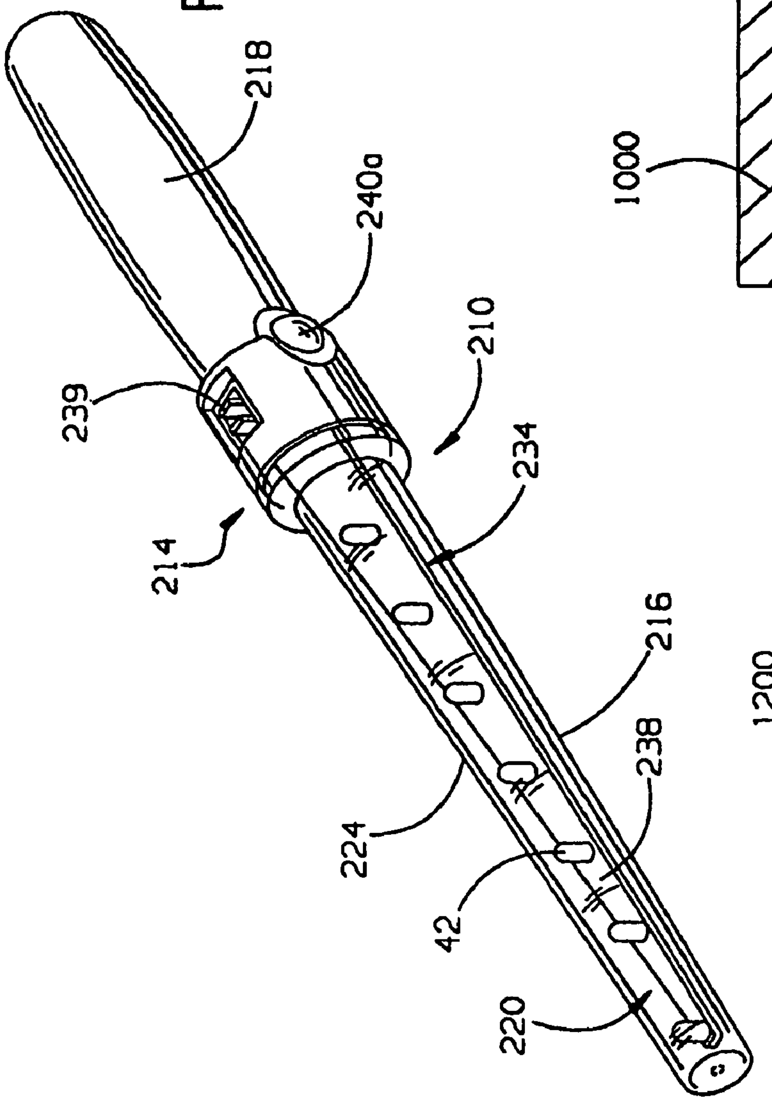
FIG. 22 is a perspective view of a battery powered light device in accordance with the present invention.
Figure 23:
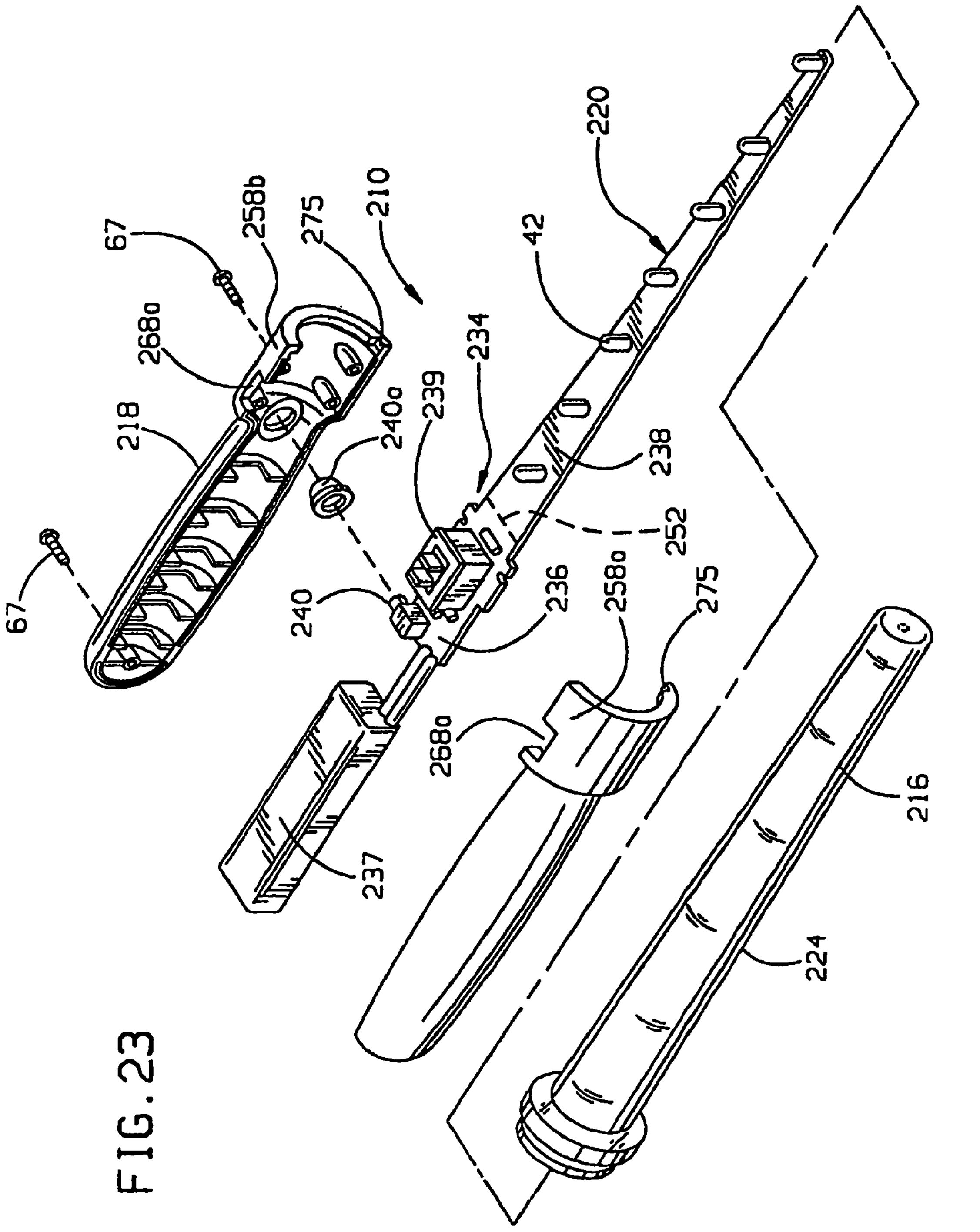
FIG. 23 is an exploded, perspective view of the light device of FIG. 22 similar to FIG. 3 showing a battery electrically connected to the printed circuit board.

Referring to FIGS. 22-23, an alternative work light 210 is illustrated. Work light 210 is similar to light 10 except that light 210 is battery powered. The work light 210 generally includes an elongate body 214 and a light source 220 therein. As with the other embodiment, the elongate body 214 includes a light-transmissive portion 216 and a handle portion 218. The light-transmissive portion 216 is formed from the same high-strength material and includes a preferred tapered configuration of a side wall portion 224 as previously described with the light 10. The discussion below highlights the differences with the battery powered light 210.

The light 210 includes a modified printed circuit board 234 having an electronics receiving base portion 236 for use with a battery and an illumination portion 238. The electronics receiving base portion 236 is truncated as compared to the electronics receiving base portion 36 because the light 210 does not need to convert 110 volt AC power to 12 volt DC power that is necessary to illuminate the preferred LEDs as the illumination source 42. In that regard, the electronics receiving portion includes a rechargeable battery 237, a recharging port 239, and a modified on/off switch 240. As illustrated, switch 240 is a push button switch having a flexible cover 240*a*; however, other types of switches may also be used. Recharging port 239 is a known type of connection to recharge the battery 237 that connects to a recharging plug (not shown) in a known manner to a wall outlet.

The light 210 also has the handle portion 218, which is similar to the handle portion 18, but is modified to accommodate both the switch 240 and the recharging port 239, which generally extend through corresponding openings of the handle 218. For example, the handle 218 is also formed from two shell members 258*a* and 258*b*. In one form, the shell member 258*b* includes two apertures 268*a* and 268*b* to receive the recharging port 239 and the on/off switch 240, respectively. In a preferred configuration, each half of the shell members 258*a* and 258*b* may also include a portion of the aperture 268*a*; therefore, when combined, the portions of opening 268*a* in each shell 258*a* and 258*b* combine to form a complete opening to receive the recharging portion 239.

Figure 24:
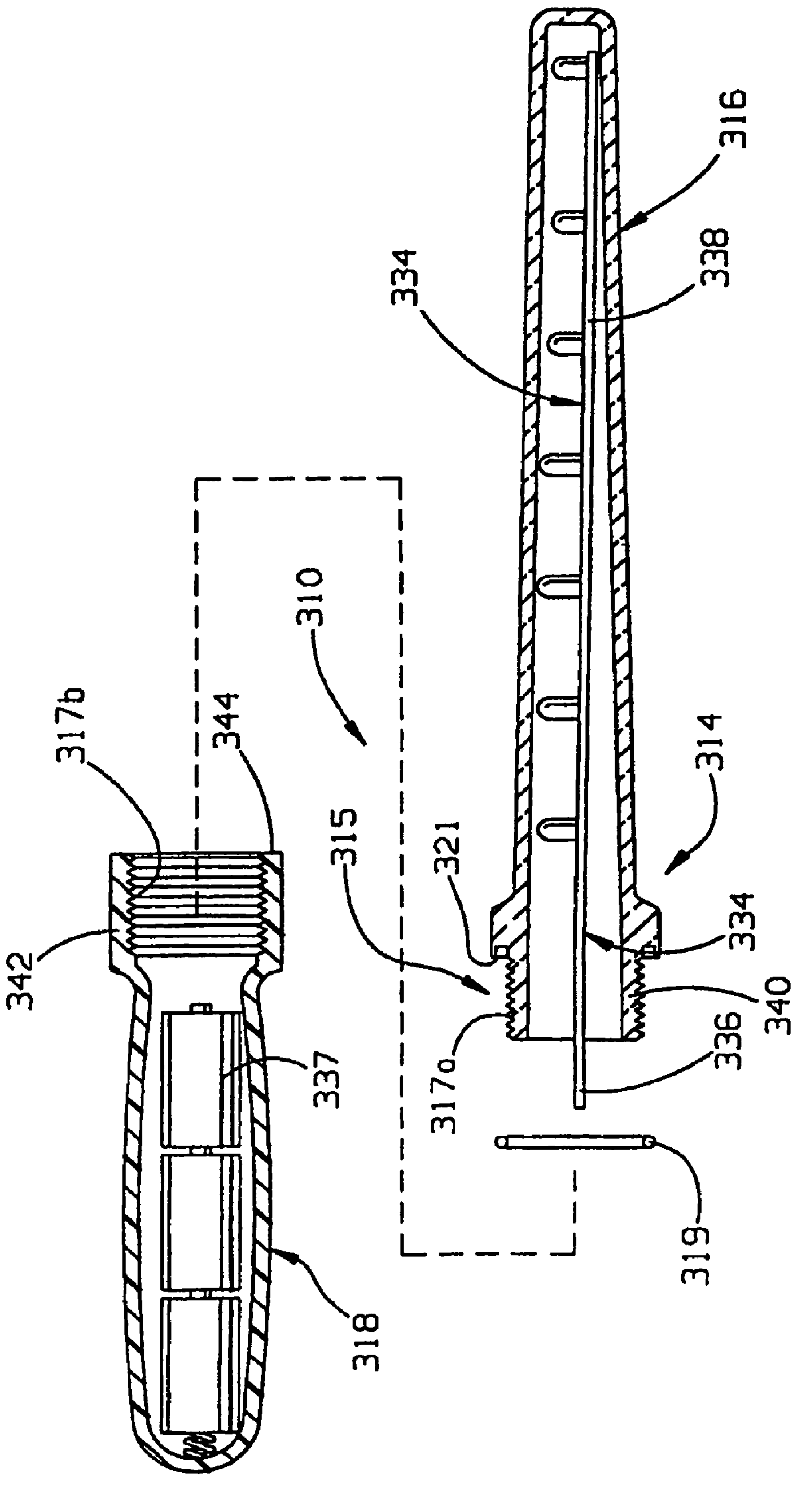
FIG. 24 is an exploded, cross-sectional, side view of another alternative light device in accordance with the present invention adapted for underwater lighting or use in hazardous environments showing a sealed threaded connection between the handle and elongate light-transmissive casing portion.

Referring to FIG. 24, another embodiment of the work light is illustrated. This embodiment is to a light 310 that includes an elongate body 314 having both a one-piece light-transmissive portion 316 and a one-piece handle portion 318. The light 310 is suitable for underwater use, in explosive environments, or other hazardous environments that may require air, vapor, or water-tight housings.

Light 310 is similar to previous described light 10 and light 210, but includes appropriate modifications so that the light is suitable in the water or explosive environments. The differences will be highlighted below. To begin with, light 310 is also battery powered, but light 310 uses standard single-use or separately rechargeable batteries 337 that are incorporated in the handle 318. The batteries 337 are in electrical communication with an electronics receiving base portion 336 of a printed circuit board 334 which is housed within handle portion. Next, the handle 218 has a one-piece construction rather than the two half shells of the previous embodiments. The one-piece construction is preferred for use in the above described wet or hazardous environments.

Additionally, to render the light 310 suitable for underwater or explosive environments, a sealed connection 315 between the handle 318 and light-transmissive portion 316 is provided. For instance, the connection 315 must substantially avoid water or gases from entering the handle 318, which could disrupt the electrical operation of the light 310. Preferably, the connection 315 uses interengaging threads 317*a* and 317*b* such that the light-transmissive portion 316 can be screwed or threaded onto the handle 318. As illustrated, the grooves 317*a* are external threads on the projecting end portion 340 of the light transmissive portion 316 and the grooves 317*b* are internal threads on an inside surface of an enlarged mounting portion 342 of the handle 318. The threads 317*a* and 317*b* mate so that the light portions can be screw threaded together. In addition, to provide a water-tight or vapor-tight seal, the connection 315 also uses a sealing member 319, such as an o-ring, gasket, or other suitable sealing member, to seal the handle 318 to the light transmissive portion 316 when threaded together. In that regard, the sealing member 319 inserted over the threaded portion 317*a* and then the light-transmissive portion 316 is screw threaded into the handle 318. The seal member 319 is then compressed between a shoulder surface 321 extending radially outward from the threaded portion 340 of the casing 316 and the end surface 344 of the handle mounting portion 342 to form the tight seal.

Figure 24A:
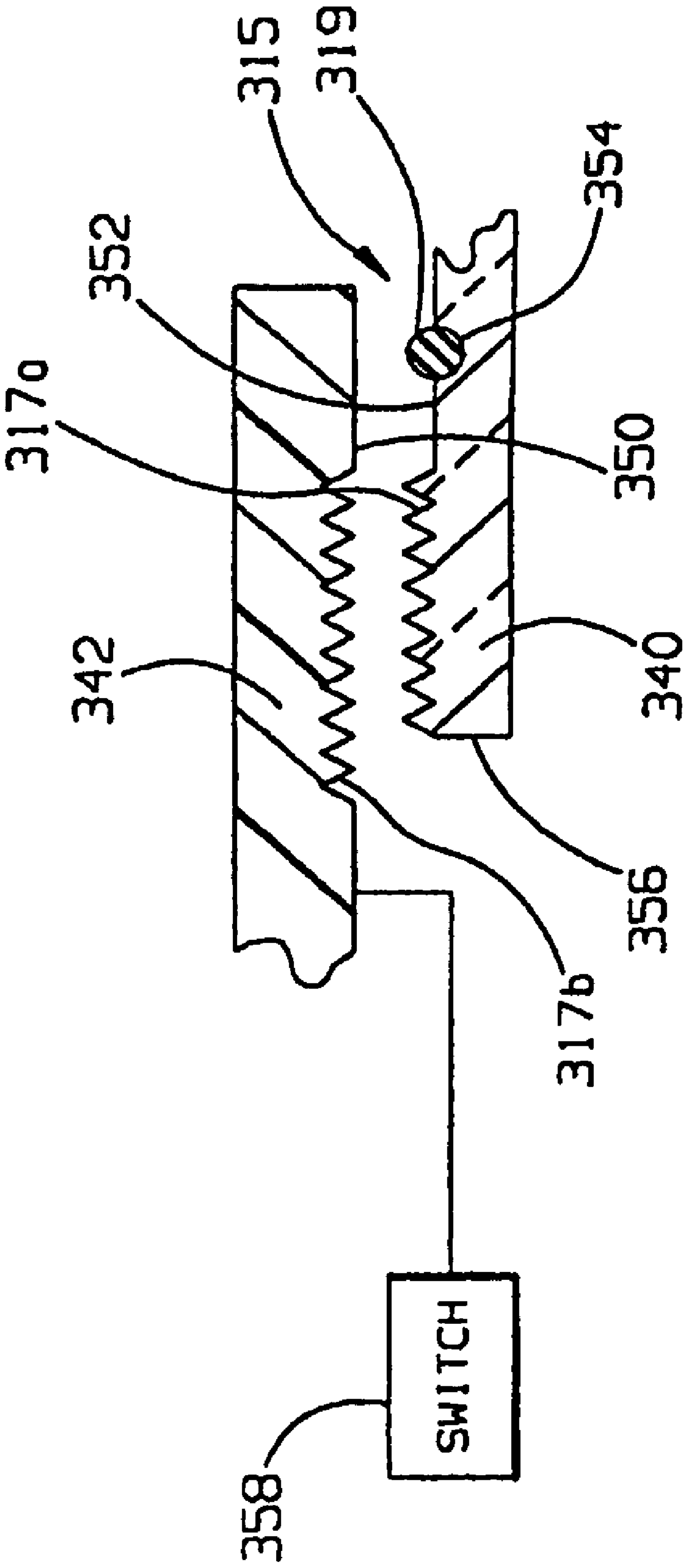
FIG. 24A is a detailed cross-sectional view of an alternative sealed threaded connection of the light device of FIG. 24.

Alternatively, as illustrated in FIG. 24A, the sealing member 319 can be disposed tightly between facing surfaces of the casing 316 and handle 318 that can shift relative to each other as the casing and handle are threaded together, such as on an inner, annular surface portion 350 of the handle mounting portion 342, and a corresponding outer, annular surface portion 352 of the light-transmissive casing end portion 340. The sealing member 319 may be seated in an annular recess 354 that extends about the casing annular surface 352. Therefore, as the casing 316 and the handle 318 are threaded to each other, as described above, the sealing member 319 is rotatively and axially translated relative to the surface portion 350 to form the sealed connection 315 between the handle 318 and light casing 316. The sealing ring member 319 is thus tightly compressed between the surfaces 350 and 352. Manifestly, the sealing member 319 could be carried on the handle 318 rather than the casing 316, as shown.

Optionally, the casing end portion 340 may operate a switch 358 in the handle 318 while maintaining the sealed connection 315 between the casing 316 and handle 318. For example, with the sealed connection 315 established, the surfaces 350 and 352 and location of the sealing member 319 therebetween are such that additional rotation in the tightening direction, as by a predetermined number of corresponding turns or fractions of a turn of the handle relative to the casing causes the casing end portion 356 to move further axially into the handle 318 to operate the switch 358. In this regard, the casing end portion 356 can include a projection that engages a switch actuator to power the light source when the requisite relative rotation of the sealed handle and casing occurs. In this configuration, the light device 310 does not require any openings or other holes in the handle 318 as with other embodiments for on/off switches or recharging ports. Once the casing 316 is threadably received by the handle 318 to form the connection 315, a substantially air-tight and/or water-tight elongate body 314 is formed having a sealed inner cavity therein. The light device 310 may be energized and de-energized by rotating the casing in a clockwise and counterclockwise direction, respectively, without breaking the air-tight and/or water-tight connection 315.

Turning to FIGS. 25-32, an alternative light device 410 is illustrated that includes one or more anti-rolling surfaces 411 to keep the light device 410 stably supported on a flat support surface such as a work surface for keeping the light device from rolling along the surface when placed thereon. The light device 410 is similar to the work light 210 as illustrated in FIGS. 22 and 23 and described in the accompanying description therewith; therefore, only the differences therefrom will be described in detail herein.

Figure 25:
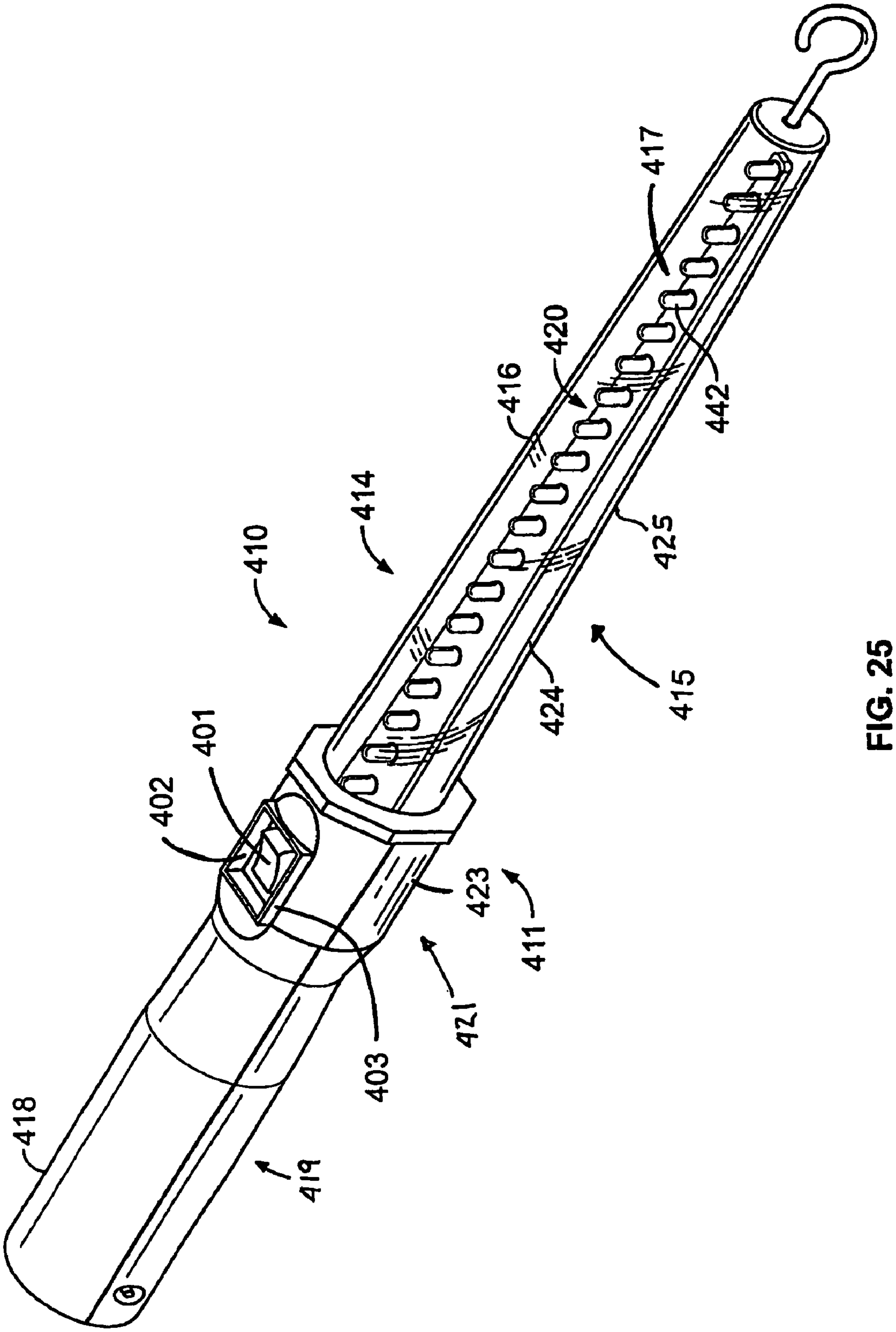
FIG. 25 is a perspective view of an alternative light device in accordance with the present invention showing an intermediate nut including anti-rolling flat surfaces thereof positioned axially between curved surfaces of a forward elongate light head and a rearward, elongate handle.

Referring initially to FIG. 25, the light device 410 includes an elongate body 414 and a light source 420. In the light device 410, the light source 420 includes an increased number of closely spaced LEDs 442 to provide an increased level of illumination. For example, the light device 410 can include between 20 and 30 or even more longitudinally aligned LEDs 442. As with the previously described light devices, the elongate body 414 of the light device 410 includes a forward, elongate light head 415 having a casing or light-transmissive portion 416 in which the light source 420 is disposed and a rearward elongate handle portion 418 for enclosing a circuit board and power source. The casing 416 preferably has the same tapered configuration for side wall portion 424 thereof as previously described with the work light 210 so as to permit the side wall portion 424 to be formed of a one-piece construction with a high strength material, as has previously been discussed.

The illustrated tapered side wall portion 424 has an annular configuration in cross-section with outer curved surface 425 of the casing 416 having a substantially constant radius of curvature. In addition, the elongate handle portion 418 has a curved, outer gripping surface 464 about a contoured, rear gripping portion 419 thereof. Accordingly, when placed on a generally flat support surface, such a light device including the described forward and rearward curved surfaces may tend to roll therealong. However, herein the anti-rolling surfaces 411 are disposed axially between the curved surfaces 425 and 464 of the casing 416 and handle portion 418, respectively. The anti-rolling surfaces 411 preferably have a flat configuration so that one of the flat surfaces 411 can be placed flush onto a flat support surface 480 (FIG. 26) keeping the light device 410 from rolling thereon.

More particularly, the anti-rolling surfaces 411 are provided about the periphery of a radially extending flange 450 between the forward light head 415 and rearward handle 418. The flange 450 is sized relative to the casing side wall 424 so that the surfaces 411 are disposed radially beyond the curved surface 425 thereof, as best seen in FIG. 29. In this manner, the surfaces 411 can engage a support surface when the device 410 is place thereon. Further, it can be seen by reference to FIGS. 28 and 30, the rear handle portion 418 has an annular wall portion 421 immediately behind or rearwardly of the flange 450. The flange 450 is sized so that the surfaces 411 are disposed radially beyond the curved, cylindrical surface 423 of the adjacent handle annular portion 421. Accordingly, when the device 410 is placed on a support surface, one of the anti-rolling surfaces 411 as well as the curved surfaces 425 and 464 of the respective casing side wall 424 and the enlarged rear handle gripping portion 419 rearward of the reduced portion 421 of the handle portion 418 engage the support surface with the engaged anti-rolling surface 411 keeping the device 410 from rolling on the support surface via the curved surfaces 425 and 464 of the device 410 engaged therewith.

It should be noted that the handle annular portion 421 has an on-off switch 401 provided in a recess 402 formed therein, as shown in FIG. 25. Raised ridges 403 extend longitudinally on either side of the recess 402. The ridges 403 are aligned with one of the flange surfaces 411 and have a height extending from the wall portion 421 sufficient so that the ridges 403 also will engage the support surface 480 when the aligned flat surface 411 is engaged therewith to provide additional stability for the elongate body 414 against rolling on the surface 480.

Figure 28:
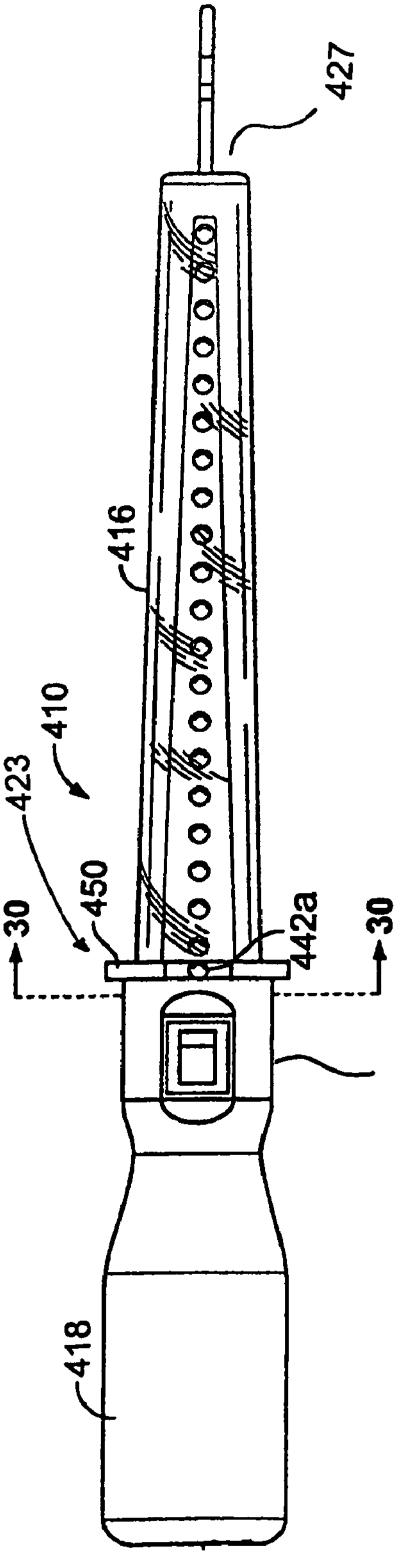
Figure 29:
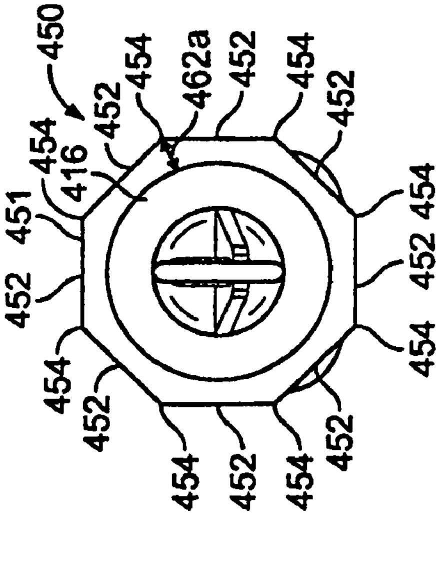
FIG. 29 is a front elevational view of the light device of FIG. 25 showing the octagonal configuration of the intermediate nut with the flat surfaces disposed radially beyond the casing.

Continuing reference to FIG. 28, the flange 450 is axially positioned along longitudinal axis X of the elongate body 414 of the device 410 closer to the rear end 423 thereof than its forward end 427. In this regard, the flange 450 can be formed integrally at the rear end 423 of the casing 416 which is axially longer than the rear handle 418.

As shown, the flange 450 has a narrow width in the axial direction so that the periphery thereof on which the anti-rolling surfaces 411 are formed extending about the longitudinal axis X with the surfaces 411 extending lengthwise in a direction transverse to axis X. More specifically, the flat, anti-rolling surfaces 411 have a length L (FIG. 31) in a direction transverse to the longitudinal axis X and a width W (FIG. 27) in the axial direction along the longitudinal axis X where the length of each flat; anti-rolling surface 411 is greater than the width thereof. By way of example and not limitation, each flat 411 can have a length L of about 10 to about 20 mm and a width of about 4 to about 6 mm; however, other sizes are suitable depending on the size of the work light.

The illustrated and preferred radially extending flange 450 is in the form of a nut-like structure 460 wherein the anti-rolling surfaces 411 are in the form of flats 452 of the nut 460 with the length L of each flat, anti-rolling surface 452 being substantially the same, and the width W of each flat, anti-rolling surface 452 being substantially the same. As shown, the lengths are preferably longer than the widths as discussed above; however, other configurations are also suitable depending on the configuration of the light device.

The nut-like structure 460 preferably has an octagonal configuration so that there are eight flats 452 circumferentially disposed about the periphery of the nut 460. The octagonal structure of the flange 450 is preferred because it is effective to minimize the amount 462 that the flats 452 thereof extend radially beyond the elongate body 414, and specifically the curved surfaces 425 and 464 of the respective casing 416 and handle 418 thereof. Similarly, corner projections 454 formed at the juncture between adjacent flats 452, which are at the maximum distance from the curved surfaces 425 and 464, also only project a minimal amount therebeyond. In this manner, the flange 450 has flat surfaces 452 thereof that generally do not include large or relatively pointed projections extending radially from the otherwise generally cylindrical body 414 of the light device 410, which could otherwise interfere with holding of the work light or otherwise provide a hindrance to the use of the light device 410. By way of example and not limitation, the corner projections 454 can be disposed at a distance 462*a* of about 4 to about 6 mm from the casing curved surface 425 (FIG. 29) and a distance 462*b* that is even less than distance 462*a* such as about 1 to about 2 mm from the adjacent handle portion 421 (FIG. 31); however, these distances may vary as needed for a particular application.

Figure 31:
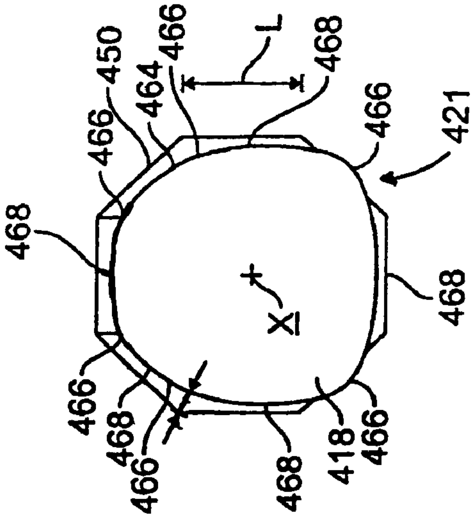
FIG. 31 is a rear elevational view of the light device of FIG. 25 showing a curved surface of the handle portion having a variable radius of curvature.
Figure 30:
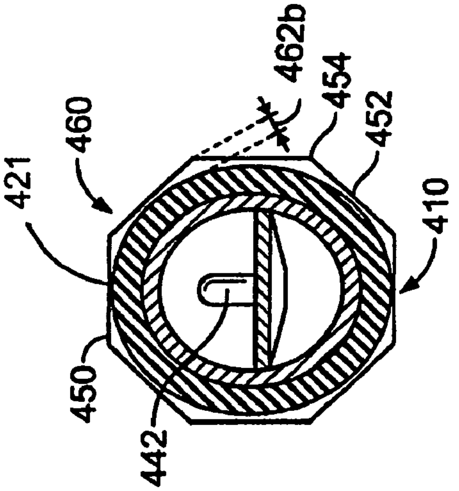
FIG. 30 is a cross sectional view taken along line 30-30 of FIG. 28 showing the nut flat surfaces disposed radially beyond an annular portion of the handle adjacent thereto.

Turning to FIG. 31, the outer surface 464 of the rear contoured gripping portion 419 has varying radius of curvature. In particular, the contoured, curved surface 464 of the handle 418 includes curved corner surface portions 466 and curved support surface portions 468 where the corner surface portions 466 are between adjacent support surface portions 468. Preferably, the support surface portions 468 have a radius of curvature larger than the corner surface portions 466.

Figure 26:
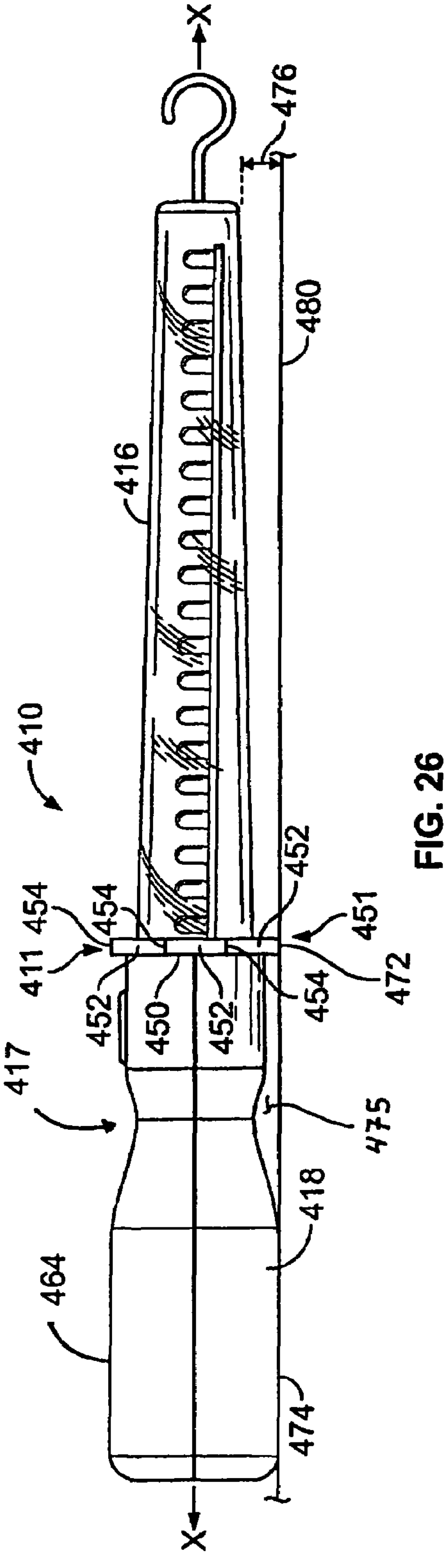
FIGS. 26-28 are elevational views of the light device of FIG. 25 showing the tapered configuration of a casing of the light head.
Figure 27:
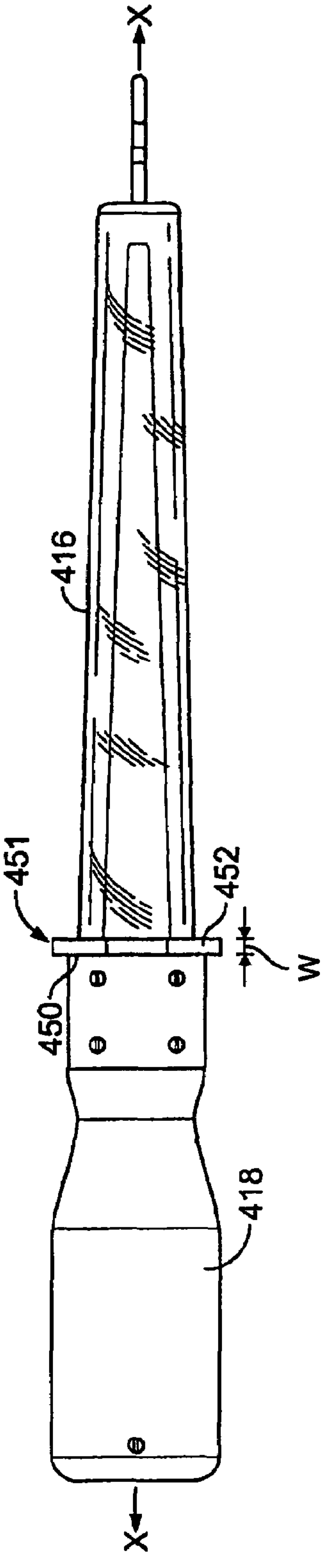

Each of the support surface portions 468 extend axially along the handle gripping portion 419 and are preferably generally circumferentially aligned with or inline axially with one of the flat, anti-rolling surfaces 452 of the radially extending flange 450. In this manner, when the light device 410 is placed on the work surface 480, one of the support surface portions 468 and the aligned flange surface 452 can cooperate to provide two areas of contact 472 and 474 between the light device 410 and the work surface 480, as illustrated in FIG. 26. It should be noted that because of the reduced size handle portion 417 axially between the handle portions 419 and 421, there will be a clearance space 475 axially between the engaged surfaces 452 and 460 with these surfaces being axially spaced from each other. As a result, one of the flats 452 and the aligned handle support surface portion 468 having a large radius of curvature, i.e., a very gentle curvature, will also cooperate with the aligned flat surface 452 to support the elongate body 414 on flat support surface 480 against rolling thereon. As shown in FIG. 26, such cooperative support enables the light device to be stably supported on the surface 480 and also positions the tapered light casing portion 418 a distance 476, e.g., approximately 6 to 7 mm, spaced above the support surface 480 at the distal end 427 thereof.

Figure 32:
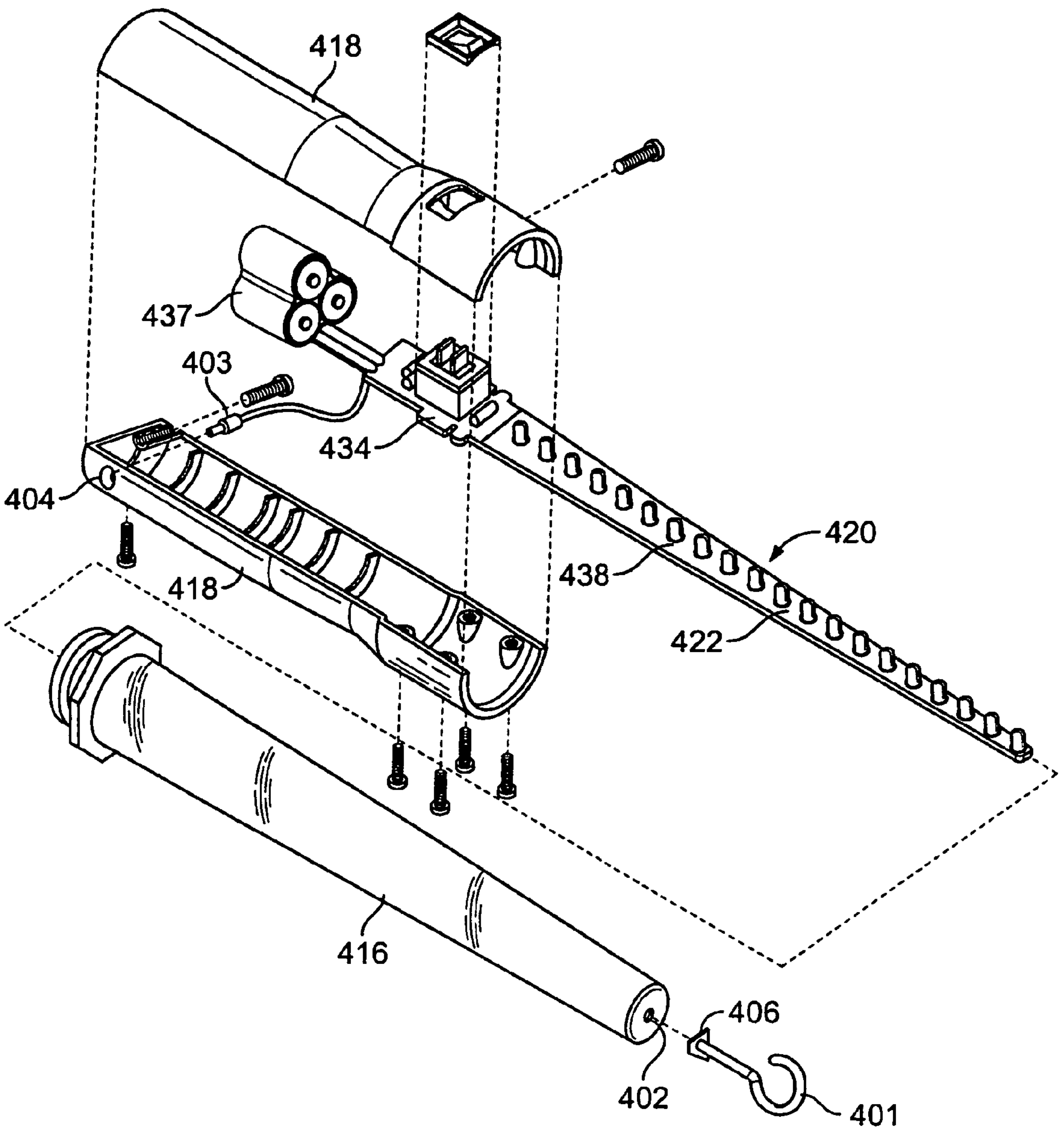
FIG. 32 is an exploded view showing the intermediate nut formed integrally in one-piece with the casing.

As best illustrated in the exploded view of FIG. 32, as previously mentioned the radially extending flange 450 may be formed integral with the casing side wall portion 424 as by molding the casing 416 including the rear nut flange 450 thereof to have a unitary, one piece construction. In this manner, the radially extending flange 450 is also formed of the same high-strength, light-transmissive material as the casing 416. With the flange formed of the light-transmissive material, one or more of the LEDs 442, such as LED 442*a* (FIG. 28), may be positioned in longitudinal alignment with the flange 450 in the interior space 417 defined by the casing side wall portion 424 to provide illumination through the flange 450 and, in particular, to provide illumination through one or more of the flat surfaces 452 thereof. Due to the generally radially thicker light-transmissive flange 450, the illumination projected therethrough is generally more diffused relative to the illumination projected through the casing portion 416. Manifestly, the radially extending flange 450 may also be molded in one piece with the handle 418 and, in this manner, could be fabricated out of an opaque or non-light transmissive material. Alternatively, the flange 450 may be a separate member secured to the light device 410, such as between the casing 416 and handle 418.

The casing 416 and handle 418 are assembled similar to the previously described light devices to form a self-contained and compact hand held lighting device that provides for stable contact on a work surface when not being held. Optionally, the light device 410 includes a holding member 401, which in one form may be a hook member as illustrated. The holding member 401 may be snap-fit in an opening 402 at a distal end 427 of the casing 416 via a barb 406 or other friction-fit type securing member. As shown, the light device 410 includes a rechargeable battery 437 to energize the light source 420 similar to the light device 210 and includes a corresponding recharging port 403 therefor extending through an aperture 404 in the handle 418; however, the light device 410 may also include non-rechargeable batteries or a plug suitable for connection to a 110 volt power source similar to the previously described light devices.

The light source 420 may include a reflective coating 422 to aid in the focusing of the illumination. By one approach, the light device 410 includes an elongate printed circuit board 434 having a illumination portion 438 extending therefrom in the light casing 416 similar to the other embodiments. The reflective coating 422 may be applied to the elongate printed circuit board 434 and, preferably, to the extending illumination portion 438 thereof that includes the one or more LEDs 424 thereon It will be understood that various changes in the details, materials, and arrangements of the parts and components that have been described and illustrated in order to explain the nature of the invention may be made by those skilled in the art within the principle and scope of the invention as expressed in the appended claims.

What is claimed is:

1. A work-light device for providing illumination to work areas, the work-light device comprising:

a generally hollow handle;

a one-piece, generally tubular illumination casing connected to the handle at one end and having an integral end wall portion distal from the handle and an integral side wall portion extending from the handle end to the distal end wall portion with the distal end wall portion extending transverse to the integral side wall portion, the end wall portion and side wall portion defining an interior space;

the side wall portion having a taper such that the illumination casing has a smaller diameter at the end portion than at the handle end;

the one-piece, generally tubular illumination casing being molded of a high-strength, substantially light-transmissive material;

a printed circuit board having a base portion mounted in the handle and an elongate portion sized to be inserted into the interior space;

smooth inner and outer surfaces of the side wall portion and end wall portion extending for the entire extent thereof from adjacent the handle end and to and including the distal end portion with at least the inner surface of the side wall portion being tapered; and a plurality of LEDs mounted to the elongate portion of the printed circuit board to extend in a radial direction generally orthogonal to the casing longitudinal axis for providing illumination radially through the smooth surfaces of the side wall portion of the illumination casing.

2. The light device of claim 1, wherein the taper of the casing side portion and the high-strength, substantially light transmissive material are selected to provide the illumination casing with strength sufficient to withstand a compression force of about 500 to about 2000 pounds per square inch.

3. The light device of claim 2, wherein the illumination casing tapers from a diameter of about 1 inch at the handle end down to a diameter of about 0.70 inch at the end portion and wherein the high-strength, substantially light-transmissive material is selected from the group consisting of polycarbonate and acrylic plastics.

4. The light device of claim 1, wherein the illumination casing tapers from a diameter of about 1 inch at the connection to the handle down to a diameter of about 0.70 inches at the end portion.

5. The light device of claim 1, wherein the high-strength, substantially light-transmissive material is selected from the group consisting of polycarbonate and acrylic.

6. The light device of claim 1, wherein the casing has a central longitudinal axis and a shoulder wall portion adjacent the handle end extending transverse to the casing axis for providing optimizing resistance to compression forces at the larger diameter handle connection.

7. The light device of claim 1, wherein the printed circuit board has proximal and distal ends and a majority of the plurality of LEDs being substantially equally spaced along the printed circuit board with a pair of distal LEDs being more closely spaced than the other LEDs for providing concentrated illumination at the distal end.

8. The light device of claim 7, wherein one of the pair of LEDs at the distal end of the printed circuit board extends generally orthogonal to the other LEDs that are aligned with each other for providing illumination in a different direction than the other, aligned LEDs.

9. A light device for providing illumination to work areas, the light device comprising:

an elongate body having opposite rearward and forward ends and a longitudinal axis extending therebetween;

a light source;

a forward, elongate light head of the elongate body having a light transmissive casing in which the light source is disposed and including a curved surface extending about the longitudinal axis with the casing extending axially forwardly to the body forward end;

a rearward elongate handle of the elongate body having a curved surface extending about the longitudinal axis with the handle extending axially rearwardly to the body rearward end; and intermediate anti-rolling surfaces axially between the curved surfaces of the forward elongate light head and rearward elongate handle and having a flat configuration to keep the elongate body from rolling on a flat support surface with one of the flat anti-rolling surfaces engaged thereon, wherein the handle curved surface has a varying radius of curvature, and the handle curved surface has corner surface portions and support surface portions with the corner surface portions being between adjacent support surface portions, and the support surface portions have a radius of curvature larger than the corner surface portions and are each generally circumferentially aligned with one of the flat, anti-rolling surfaces to provide additional stability against rolling.

10. The light device of claim 9 wherein the casing includes a rearward, radially extending flange that has a periphery extending about the longitudinal axis and on which the flat, anti-rolling surfaces are formed with the flange being sized relative to the curved surfaces of the light head and the handle so that one of the flat surfaces thereof will engage on the support surface with the elongate body placed thereon.

11. The light device of claim 9 wherein the flat surfaces have corner projections between adjacent flat surfaces with the corner projections extending radially beyond the curved surfaces of the forward light head and rearward handle.

12. The light device of claim 9 wherein the casing curved surface has a substantially constant radius of curvature.

13. The light device of claim 9 wherein the flat, anti-rolling surfaces have a length in a direction transverse to the longitudinal axis and a width in an axial direction along the longitudinal axis with the length of each flat, anti-rolling surface being greater than the width thereof.

14. The light device of claim 13 wherein the lengths of each of the flat, anti-rolling surfaces are the same, and the widths of each of the flat, anti-rolling surfaces are the same.

15. The light device of claim 9 wherein the flat, anti-rolling surfaces form a nut-like structure adjacent a forward end of the handle.

16. The light device of claim 15 wherein the nut-like structure has an octagonal configuration so that there are eight flat, anti-rolling surfaces thereon.

17. A light device for providing illumination to work areas, the light device comprising:

an elongate body having a longitudinal axis;

a light source;

an elongate, tubular light transmissive casing of the body in which the light source is disposed for emanating light generally radially out therefrom;

a curved surface of the casing extending about the longitudinal axis;

an elongate handle of the body having a curved surface extending about the longitudinal axis; and an intermediate nut having flats thereof between the casing and the handle with the nut being sized so that with the elongate body placed on a flat support surface, one of the nut flats will engage flush thereon to keep the curved surfaces of the body from rolling on the support surface, wherein the curved surface of the elongate handle includes longitudinally extending surface portions generally circumferentially aligned with the flats with the surface portions including side surface portions and corner surface portions between the side surface portions, the side surface portions having a greater radius of curvature than the corner surface portions for cooperating with the aligned flats to stably support the elongate body against rolling on the support surface.

18. The light device of claim 17 wherein the curved surface of the casing has a substantially constant radius of curvature, and the nut is radially enlarged relative to the casing so that the flats are disposed beyond the casing curved surface.

19. The light device of claim 17 wherein the casing is tapered to have a large diameter end adjacent the intermediate nut tapering down to a small diameter distal end of the casing, and the nut has an octagonal configuration so that there are eight flats thereof that each project beyond the adjacent casing large diameter end by a minimal amount.

20. The light device of claim 17 wherein the nut includes corners between the flats thereof that project radially beyond the handle curved surface.

21. The light device of claim 20 wherein the nut has an octagonal configuration so that there are eight flats thereof and the corners only project beyond the handle curved surface by a minimal distance.

22. The light device of claim 17 wherein the casing and nut are of an integral, one-piece construction.

* * * * *

UNITED STATES PATENT AND TRADEMARK OFFICE

CERTIFICATE OF CORRECTION

PATENT NO. : 7,703,966 B2
APPLICATION NO. : 12/001468
DATED : April 27, 2010
INVENTOR(S) : Michael Waters It is certified that error appears in the above-identified patent and that said Letters Patent is hereby corrected as shown below:

Claim 1, Column 19, Line 29, delete “end” and insert -- end wall --.

Signed and Sealed this

Thirty-first Day of August, 2010

David J. Kappos

*Director of the United States Patent and Trademark Office*